US 8,592,576 B2

(12) United States Patent
Howard et al.

(10) Patent No.: US 8,592,576 B2
(45) Date of Patent: Nov. 26, 2013

(54) UNSYMMETRICAL PYRROLOBENZODIAZEPINE-DIMERS FOR TREATMENT OF PROLIFERATIVE DISEASES

(75) Inventors: Philip Wilson Howard, London (GB); Stephen John Gregson, London (GB); Luke Masterson, London (GB)

(73) Assignee: Spirogen Sarl, St-Legier-la Chiesaz (CH)

( * ) Notice: Subject to any disclaimer, the term of this patent is extended or adjusted under 35 U.S.C. 154(b) by 184 days.

(21) Appl. No.: 13/123,327

(22) PCT Filed: Oct. 16, 2009

(86) PCT No.: PCT/GB2009/002498
§ 371 (c)(1), (2), (4) Date: Apr. 8, 2011

(87) PCT Pub. No.: WO2010/043880
PCT Pub. Date: Apr. 22, 2010

(65) Prior Publication Data
US 2011/0196148 A1    Aug. 11, 2011

(30) Foreign Application Priority Data
Oct. 17, 2008 (GB) .................................... 0819095.1

(51) Int. Cl.
C07D 487/04 (2006.01)
(52) U.S. Cl.
USPC .......................................................... 540/496
(58) Field of Classification Search
None
See application file for complete search history.

(56) References Cited

U.S. PATENT DOCUMENTS

| | | | |
|---|---|---|---|
| 3,523,941 A | 8/1970 | Leimgruber et al. | |
| 3,524,849 A | 8/1970 | Batcho et al. | |
| 4,185,016 A | 1/1980 | Takanabe et al. | |
| 4,239,683 A | 12/1980 | Takanabe et al. | |
| 4,309,437 A | 1/1982 | Ueda et al. | |
| 5,418,241 A | 5/1995 | Jegham et al. | |
| 6,562,806 B1 | 5/2003 | Thurston et al. | |
| 6,608,192 B1 | 8/2003 | Thurston et al. | |
| 6,660,856 B2 | 12/2003 | Wang | |
| 6,747,144 B1 | 6/2004 | Thurston et al. | |
| 6,909,006 B1 | 6/2005 | Thurston et al. | |
| 7,049,311 B1 | 5/2006 | Thurston et al. | |
| 7,067,511 B2 | 6/2006 | Thurston et al. | |
| 7,265,105 B2 | 9/2007 | Thurston et al. | |
| 7,407,951 B2 | 8/2008 | Thurston et al. | |
| 7,429,658 B2 | 9/2008 | Howard et al. | |
| 7,528,126 B2 | 5/2009 | Howard et al. | |
| 7,557,099 B2 | 7/2009 | Howard et al. | |
| 7,612,062 B2 | 11/2009 | Howard et al. | |
| 7,704,924 B2 | 4/2010 | Thurston et al. | |
| 7,741,319 B2 * | 6/2010 | Howard et al. | 514/220 |
| 2003/0195196 A1 | 10/2003 | Thurston et al. | |
| 2004/0138269 A1 | 7/2004 | Sun et al. | |
| 2004/0198722 A1 | 10/2004 | Thurston et al. | |
| 2007/0072846 A1 | 3/2007 | Vishnuvajjala et al. | |
| 2007/0191349 A1 | 8/2007 | Howard et al. | |
| 2007/0249591 A1 | 10/2007 | Howard et al. | |
| 2008/0090812 A1 | 4/2008 | Pepper et al. | |
| 2008/0214525 A1 | 9/2008 | Howard et al. | |
| 2010/0113425 A1 | 5/2010 | Howard et al. | |
| 2011/0160192 A1 | 6/2011 | Howard et al. | |

FOREIGN PATENT DOCUMENTS

| | | |
|---|---|---|
| EP | 1193270 | 4/2002 |
| FR | 2027356 | 12/1969 |
| FR | 2586683 | 3/1987 |
| GB | 1299198 | 12/1972 |

(Continued)

OTHER PUBLICATIONS

Gregson et al., caplus an 2006:1124678.*

(Continued)

*Primary Examiner* — Sun Jae Loewe
(74) *Attorney, Agent, or Firm* — Michael Best & Friedrich LLP

(57) ABSTRACT

Claimed are unsymmetrical Pyrrolobenzodiazepine-dimers (PBD-dimers) of formula (I), that are unsymmetrical due at least to the values that the variables $R^{12}$ and $R^2$ represent. Formula (I), wherein: $R^2$ is of formula (II), where A is a $C_{5-7}$ aryl group, X is selected from the group comprising: OH, SH, $CO_2H$, COH, N=C=O, $NHR^N$, wherein $R^N$ is selected from the group comprising H and $C_{1-4}$ alkyl, and $(OC_2H_4)_mOCH_3$, where m is 1 to 3, and either: (i) $Q^1$ is a single bond, and $Q^2$ is selected from a single bond and $-Z-(CH_2)_n-$, where Z is selected from a single bond, O, S and NH and n is from 1 to 3; or (ii) $Q^1$ is $-CH=CH-$, and $Q^2$ is a single bond; $R^{12}$ is a $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene. The other variables are as defined in the claims. The compounds are useful for the treatment of proliferative diseases.

42 Claims, No Drawings

(56) References Cited

FOREIGN PATENT DOCUMENTS

| | | |
|---|---|---|
| GB | 2053894 | 2/1981 |
| JP | 53-82792 | 7/1978 |
| JP | 57131791 | 8/1982 |
| JP | 58180487 | 10/1983 |
| WO | WO 92/19620 D | 11/1992 |
| WO | WO 93/18045 | 9/1993 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/110423 | 11/2005 |
| WO | WO 2006/111759 | 10/2006 |

OTHER PUBLICATIONS

ClinicalTrial, 2011, http://www.nature.com/news/2011/110928/full/477526a.html.*
Cancer, 2012, http://wiki.answers.com/Q/How_many_different_types of cancer are there.*
Cancer2, 2012, http://en.wikipedia.org/wiki/Management of cancer.*
Berge et al., "Pharmaceutical salts," J. Pharm. Sci. (1977) 66:1-19.
Dong, Q. et al., "Reductive cleavage of TROC groups under neutral conditions with cadmium-lead couple," Tetrahedron Lett. (1995) 36(32):5681-5682.
Fey, T. et al., "Silica-supported TEMPO catalysts: synthesis and application in the anelli oxidation of alcohols," J. Org. Chem. (2001) 66:8154-8159.
Greene, T.W. et al., Protective Groups in Organic Synthesis, John Wiley & Sons (1999) 3rd ed., 23-200, 503-549, 633-647.
Hartley, J.A. et al., "SG2285, a novel C2-aryl-substituted pyrrolobenzodiazepine dimer prodrug that cross-links DNA and exerts highly potent antitumor activity," Cancer Res. (2010) 70(17):6849-6858.
Banker, G.S. et al., Modern Pharmaceutics, Third Edition, Marcel Dekker, New York (1996) 451 and 596.
Dorwald, F.Z., Side Reactions in Organic Synthesis: a Guide to Successful Synthesis Design, Weinheim: Wiley-VCH Verlag GmbH and Co., KGaA (2005) Preface.
Gavezzotti, A., "Are crystal structures predictable?" Acc. Chem. Res. (1994) 27:309-314.
Jordan, V.C., "Tamoxifen: a most unlikely pioneering medicine," Nature Reviews: Drug Discovery (2003) 2:205-213.
Souillac, P. et al., "Characterization of delivery systems, differential scanning calorimetry," Encyclopedia of Controlled Drug Delivery (1999) 212-227.
Vippagunta, S.R. et al., "Crystalline solids," Adv. Drug Delivery Rev. (2001) 48:3-26.
Wolff, M.E., Burger's Medicinal Chemistry, 5th Edition, Part I, John Wiley & Sons, New York (1995) 975-977.
Adams et al., "Molecular modelling of a sequence-specific DNA-binding agent based on the pyrrolo[2,1-c][1,4]benzodiazepines," Pharm. Pharmacol. Commun. (1999) 5:555-560.
Alley, M.C. et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.
Althius, T. H. and Hess, H. J., "Synthesis and Identification of the Major Metabolites of Prazosin Formed in Dog and Rat," J. Medicinal Chem. (1977) 20(1):146-148.
Arima et al., "Studies on Tomaymycin, a New Antibiotic. I. Isolation and Properties of Tomaymycin," J. Antibiotics (1972) 25:437-444.

Berry, J. M. et al., "Solid-phase synthesis of DNA-interactive pyrrolo[2,1-c][1,4]benzodiazepines," Tetrahedron Letters (2000) 41:6171-6174.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.
Cooper, N. et al., "Synthesis of novel PBDs as anti-tumour agents," Chem. Commun. (2002) 16:1764-1765.
Courtney, S. M. et al., "A new convenient procedure for the synthesis of pyrrolo[2,1-c][1,4]benzodiazepines", Tetrahedron Letters, vol. 34, No. 33, 5327-28 (1993).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Dupont, C. et al., "Synthesis of rhazinilam analogue acting as an inhibitor of tubulin assembly," Tetrahedron Lett. (2000) 41:5853-5856.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).
Firsching, A. et al., "Antiproliferative and angiostatic activity of suramin analogues," Cancer Res. (1995) 55:4957-4961.
Foloppe, M.P. et al., "DNA-binding properties of pyrrolo[2,1-c][1,4]benzodiazephine N10-C11 amidines," Eur. J. Med. Chem., 31, 407-410 (1996).
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Greene, T.W. and Wuts, P.G.M., Protective Groups in Organic Synthesis, John Wiley & Sons, 2nd ed., Ch 7, 315-345 (1991).
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

(56) References Cited

OTHER PUBLICATIONS

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J. Med. Chem.*, 44: 737-748 (2001).
Gregson, S.J. et al., "Effect of C2-*exo* Unsaturation on the Cytotoxicity and DNA-Binding Reactivity of Pyrrolo[2,1-c]1,4]benzodiazepines", *Bioorganic & Medicinal Chemistry Letters*, 10: 1845-1847 (2000).
Guiotto, A. et al., "Synthesis of novel C7-aryl substituted pyrrolo[2,1-c][1,4]benzodiazepines (PBDs) via Pro-N10-troc protection and suzuki coupling," *Bioorganic & Medicinal Chemistry Letters*, 8, No. 21, 3017-3018 (1998).
Hara et al., "DC 102, a new glycosidic pyrrolo(1,4)benzodiazepine antibiotic produced by *streptomyces* sp.", *J. Antibiotics*, 41, 702-704 (1988).
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hochlowski, J. et al., "Abbeymycin, a new anthramycin-type antibiotic produced by a streptomycete," *J. Antibiotics*, 40, 145-148 (1987).
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.
Howard, P.W. et al., "Synthesis of a novel C2/C2'-aryl-substituted pyrrolo[2,1-c][1,4]benzodiazepine dimmer prodrug with improved water solubility and reduced DNA reaction rate," Bioorg. Med. Chem. (2009) In Press, 4 pages.
Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).
Itoh et al., "Sibanomicin, a new pyrrolo(1,4)benzodiazepine antitumor antibiotic produced by a *micromonospora* sp." *J. Antibiotics*, 41, 1281-1284 (1988).
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., et al., "An Efficient Synthesis of Pyrrolo[2,1-c][1,4] Benzodiazepine Antibiotics via Reductive Cyclization," *Bioorg. Med. Chem. Ltrs*, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", *Tetrahedron*, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1688-1689.
Kohn, K., "Anthramycin," *Antibiotics III*, Springer-Verlag, NY, 3-11 (1975).
Konishi, M. et al., "Chicamycin, a new antitumor antibiotic II. Structure determination of chicamycins A and B," *J. Antibiotics*, 37, 200-206 (1984).
Kunimoto et al., "Mazethramycin, a new member of anthramycin group antibiotics," *J. Antibiotics*, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Leber, J.D. et al., "A revised structure for sibiromycin," *J. Am. Chem. Soc.*, 110, 2992-2993 (1988).
Leimgruber, W. et al., "Isolation and characterization of anthramycin, a new antitumor antibiotic," *J. Am. Chem. Soc.*, 87, 5791-5793 (1965).
Leimgruber, W. et al., "The structure of anthramycin," *J. Am. Chem. Soc.*, 87, 5793-5795 (1965).
Leimgruber, W. et al., "Total synthesis of anthramycin," *J. Am. Chem. Soc.*, 90, 5641-5643 (1968).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Mori, M. et al., "Total syntheses of prothracarcin and tomaymycin by use of palladium catalyzed carbonylation," Tetrahedron (1986) 42(14):3793-3806.
Mountzouris, J.A. et al., "Comparison of a DSB-120 DNA interstrand cross-linked adduct with the corresponding bis-Tomamycin adduct," J. Med. Chem. (1994) 37:3132-3140.
Nagasaka, T. and Koseki, Y, "Stereoselective Synthesis of Tilivalline," *Journal of Organic Chemistry*, vol. 63, No. 20, 6797-6801 (1998).
Nagasaka, T. et al., "Stereoselective Synthesis of Tilivalline," *Tetrahedron Letters*, 30:14, 1871-1872 (1989).
O'Neil, Chemical Abstract No. 171573p, "The synthesis of Functionalized Pyrrolo-[2,1-c][1,4]-Benzodiazepines", *Chemical Abstracts*, vol. 126, No. 13, 618 (1997).
O'Neil, I.A., et al., "The Synthesis of Functionalized Pyrrolo-[2,1-c][1,4]-Benzodiazepines," *Synlett*, 75-78 (1997).
O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).
Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).
Shimizu, K et al., "Prothracarcin, a Novel Antitumor Antibiotic," *J. Antibiotics*, 35, 972-978 (1982).
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Suggs, J.W. et al., "Synthesis and structure of anthramycin analogs via hydride reduction of dilactams," *Tetrahedron Letters*, 26, No. 40, 4871-4874 (1985).
Takeuchi, T. et al., "Neothramycins A and B, New Antitumor Antibiotics," *J. Antibiotics*, 29, 93-96 (1976).
Tercel, M. et al., "Unsymmetrical DNA cross-linking agents: combination of the CBI and PBD pharmacophores," J. Med. Chem. (2003) 46:2132-2151.
Thurston, D. E., "Advances in the study of Pyrrolo[2,1-c][1,4] benzodiazepine (PBD) Antitumour Antibiotics", *Molecular Aspects of Anticancer Drug-DNA Interaction*, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," *Chem. Brit.*, 26, 767-772 (1990).

(56) References Cited

OTHER PUBLICATIONS

Thurston, D.E. et al., "Effect of A-ring modifications on the DNA-binding behavior and cytotoxicity of pyrrolo[2,1-c][1,4]benzodiazepines", *Journal of Medicinal Chemistry*, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tsunakawa, M. et al., "Porothramycin, a new antibiotic of the anthramycin group: Production, isolation, structure and biological activity," *J. Antibiotics*, 41:1366-1373 (1988).
Umezawa, H. et al., "Mazethramycins," *SciFinder Scholar*, 2-3 (2002).
Umezawa, H. et al., Chemical Abstract No. 4427a, "Mazethramycins" *Chemical Abstracts*, vol. 90, No. 1, 428 (1979).
Weidner-Wells, M.A. et al., "Photochemical approach to the synthesis of the pyrrolo[1,4]benzodiazepine antibiotics," J. Org. Chem. (1989) 54:5746-5758.
Wilson, S.C. et al., "Design and Synthesis of a Novel Epoxide-Containing Pyrrolo[2,1-c][1,4]benzodiazepine (PBD) via a New Cyclization Procedure," *Tetrahedron Letters*, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", *J. Med. Chem.* 42:4028-4041 (1999).
Wolff, M.E., Burger's Medicinal Chemistry, 4th Edition, Part I, Wiley: New York (1979) 336-337.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
United States Office Action for U.S. Appl. No. 10/598,518 dated Mar. 13, 2009 (7 pages).
United States Office Action for U.S. Appl. No. 10/598,518 dated Sep. 28, 2009 (6 pages).
United States Patent Office Action for U.S. Appl. No. 12/610,478 dated Aug. 6, 2010 (14 pages).
United States Patent Office Action for U.S. Appl. No. 12/610,478 dated Dec. 17, 2010 (5 pages).
United States Office Action for U.S. Appl. No. 09/763,813 dated Sep. 10, 2002 (11 pages).
United States Office Action for U.S. Appl. No. 09/763,813 dated Feb. 28, 2003 (8 pages).
United States Office Action for U.S. Appl. No. 09/763,813 dated May 21, 2003 (7 pages).
United States Office Action for U.S. Appl. No. 09/763,767 dated May 23, 2002 (20 pages).
United States Office Action for U.S. Appl. No. 09/763,767 dated Nov. 15, 2002 (19 pages).
United States Office Action for U.S. Appl. No. 09/763,767 dated May 20, 2003 (11 pages).
United States Office Action for U.S. Appl. No. 09/763,767 dated Jan. 14, 2004 (11 pages).
United States Office Action for U.S. Appl. No. 09/763,767 dated Aug. 4, 2004 (7 pages).
United States Office Action for U.S. Appl. No. 09/763,767 dated Jun. 9, 2005 (5 pages).
United States Office Action for U.S. Appl. No. 11/367,241 dated Jun. 22, 2006 (11 pages).
United States Office Action for U.S. Appl. No. 11/367,241 dated Nov. 24, 2006 (16 pages).
United States Office Action for U.S. Appl. No. 09/763,814 dated Sep. 13, 2001 (16 pages).
United States Office Action for U.S. Appl. No. 09/763,814 dated Apr. 23, 2002 (23 pages).
United States Office Action for U.S. Appl. No. 09/763,814 dated Jul. 24, 2002 (8 pages).
United States Office Action for U.S. Appl. No. 09/763,814 dated Sep. 23, 2002 (8 pages).
United States Office Action for U.S. Appl. No. 09/673,768 dated Dec. 14, 2001 (7 pages).
United States Office Action for U.S. Appl. No. 09/673,768 dated Jul. 12, 2002 (4 pages).
United States Office Action for U.S. Appl. No. 09/673,768 dated Dec. 24, 2002 (4 pages).
United States Office Action for U.S. Appl. No. 10/021,213 dated May 20, 2003 (10 pages).
United States Office Action for U.S. Appl. No. 10/379,049 dated Mar. 21, 2005 (14 pages).
United States Office Action for U.S. Appl. No. 10/379,049 dated Oct. 5, 2005 (17 pages).
United States Office Action for U.S. Appl. No. 10/379,049 dated Apr. 26, 2006 (9 pages).
United States Office Action for U.S. Appl. No. 10/602,521 dated Sep. 24, 2007 (12 pages).
United States Office Action for U.S. Appl. No. 10/602,521 dated Mar. 26, 2008 (8 pages).
United States Office Action for U.S. Appl. No. 10/602,521 dated May 31, 2008 (8 pages).
United States Office Action for U.S. Appl. No. 10/602,521 dated Jul. 15, 2008 (7 pages).
United States Office Action for U.S. Appl. No. 10/602,521 dated Dec. 10, 2008 (12 pages).
United States Office Action for U.S. Appl. No. 10/602,521 dated Sep. 9, 2009 (14 pages).
United States Office Action for U.S. Appl. No. 10/824,743 dated Jul. 31, 2006 (6 pages).
United States Office Action for U.S. Appl. No. 10/824,743 dated Jan. 17, 2007 (15 pages).
United States Office Action for U.S. Appl. No. 10/824,743 dated Oct. 9, 2007 (12 pages).
United States Office Action for U.S. Appl. No. 10/534,825 dated Sep. 7, 2006 (7 pages).
United States Office Action for U.S. Appl. No. 10/534,825 dated Mar. 2, 2007 (7 pages).
United States Office Action for U.S. Appl. No. 10/534,825 dated Sep. 20, 2007 (4 pages).
United States Office Action for U.S. Appl. No. 10/571,274 dated Oct. 31, 2007 (6 pages).
United States Office Action for U.S. Appl. No. 10/598,470 dated May 23, 2008 (6 pages).
United States Office Action for U.S. Appl. No. 10/598,482 dated May 22, 2008 (9 pages).
United States Office Action for U.S. Appl. No. 10/598,482 dated Nov. 24, 2008 (6 pages).
United States Office Action for U.S. Appl. No. 10/598,691 dated Mar. 21, 2008 (7 pages).
United States Office Action for U.S. Appl. No. 10/598,691 dated Sep. 29, 2008 (6 pages).
United States Office Action for U.S. Appl. No. 10/591,140 dated Jul. 6, 2009 (17 pages).
United States Patent Office Action for U.S. Appl. No. 10/591,140 dated Jan. 19, 2010 (7 pages).
United States Patent Office Action for U.S. Appl. No. 10/591,140 dated Dec. 6, 2010 (7 pages).
United States Patent Office Action for U.S. Appl. No. 13/041,849 dated Dec. 1, 2011 (24 pages).

(56) References Cited

OTHER PUBLICATIONS

United States Patent Office Action for U.S. Appl. No. 13/041,849 dated Jun. 6, 2012 (13 pages).
United States Office Action for U.S. Appl. No. 11/569,007 dated Oct. 15, 2008 (12 pages).
United States Office Action for U.S. Appl. No. 11/569,007 dated Jun. 1, 2009 (10 pages).
United States Patent Office Action for U.S. Appl. No. 12/089,459 dated Oct. 14, 2010 (13 pages).
United States Patent Office Action for U.S. Appl. No. 12/089,459 dated Apr. 12, 2011 (7 pages).
United States Office Action for U.S. Appl. No. 12/089,459 dated Aug. 17, 2011 (3 pages).
United States Patent Office Action for U.S. Appl. No. 12/610,478 dated Jul. 22, 2011 (7 pages).
United States Patent Office Action for U.S. Appl. No. 13/041,849 dated Aug. 22, 2012 (8 pages).
Sutherland, M.S.K. et al., "SGN-CD33A: a novel CD33-directed antibody-drug conjugate, utilizing pyrrolobenzodiazepine dimers, demonstrates preclinical antitumor activity against multi-drug resistant human AML," American Society of Hematology (Dec. 8-12, 2012) Atlanta, Georgia, Abstract No. 3589.

\* cited by examiner

UNSYMMETRICAL PYRROLOBENZODIAZEPINE-DIMERS FOR TREATMENT OF PROLIFERATIVE DISEASES

CROSS-REFERENCE TO RELATED APPLICATIONS

This patent application is a national stage filing under 35 U.S.C. 371 of International Application No. PCT/GB2009/002498, filed on Oct. 16, 2009, which claims foreign priority benefits to United Kingdom Patent Application No. 0819095.1, filed Oct. 17, 2008. These applications are incorporated herein by reference in their entireties.

The present invention relates to pyrrolobenzodiazepines (PBDs), in particular pyrrolobenzodiazepine dimers having a C2-C3 double bond and an aryl group at the C2 position in each monomer unit.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

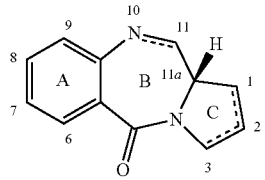

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III.* Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

It has been previously disclosed that the biological activity of this molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity. One example of a PBD dimmer, SG2000 (SJG-136):

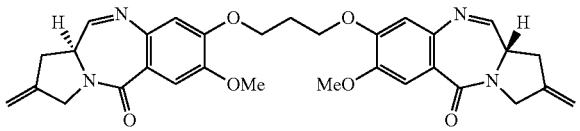

has recently completed Phase I clinical trials in the oncology area and is about to enter Phase II (Gregson, S., et al., *J. Med. Chem.*, 44, 737-748 (2001); Alley, M. C., et al., *Cancer Research*, 64, 6700-6706 (2004); Hartley, J. A., et al., *Cancer Research*, 64, 6693-6699 (2004)).

More recently, the present inventors have previously disclosed in WO 2005/085251, dimeric PBD compounds bearing C2 aryl substituents, such as SG2202 (ZC-207):

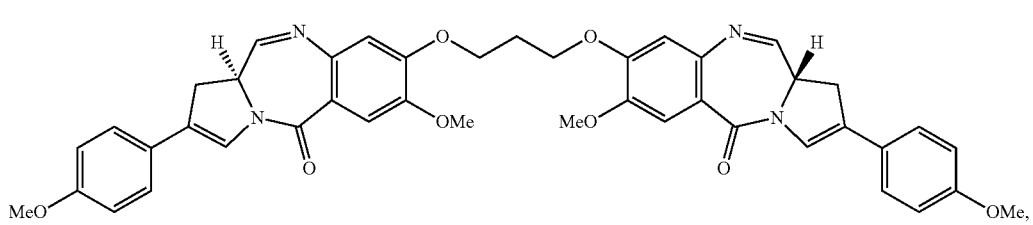

and in WO2006/111759, bisulphites of such PBD compounds, for example SG2285 (ZC-423):

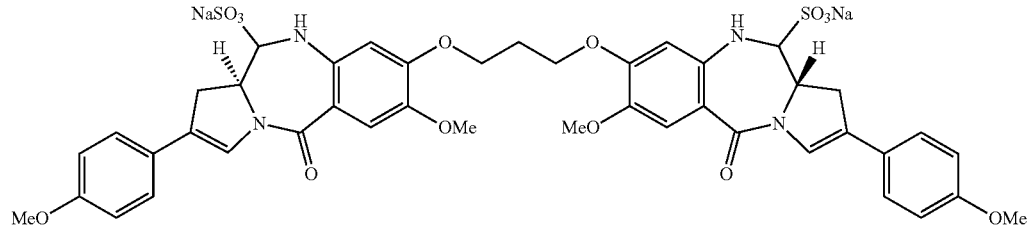

ZC-423

These compounds have been shown to be highly useful cytotoxic agents (Howard, P. W., et al., *Bioorg. Med. Chem.* (2009), doi: 10.1016/j.bmcl.2009.09.012).

Due to the manner in which these highly potent compounds act in cross-linking DNA, these molecules have been made symmetrically. This provides for straightforward synthesis, either by constructing the PBD moieties simultaneously having already formed the dimer linkage, or by reacting already constructed PBD moieties with the dimer linking group.

DISCLOSURE OF THE INVENTION

The present inventors have developed an unsymmetrical dimeric PBD compound bearing aryl groups in the C2 position of each monomer, where one of these groups bears a substituent designed to provide an anchor for linking the compound to another moiety.

The present invention comprises a compound with the formula I:

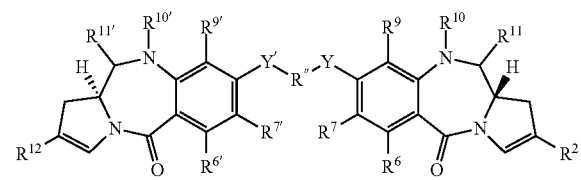

I wherein:
$R^2$ is of formula II:

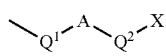

II where A is a $C_{5-7}$ aryl group, X is selected from the group comprising: OH, SH, $CO_2H$, COH, N=C=O, $NHR^N$, wherein $R^N$ is selected from the group comprising H and $C_{1-4}$ alkyl, and $(OC_2H_4)_mOCH_3$, where m is 1 to 3, and either:
(i) $Q^1$ is a single bond, and $Q^2$ is selected from a single bond and —Z—$(CH_2)_n$, where Z is selected from a single bond, O, S and NH and is from 1 to 3; or
(ii) $Q^1$ is —CH=CH—, and $Q^2$ is a single bond;
$R^{12}$ is a $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NHRR', nitro, $Me_3Sn$ and halo; either:
(a) $R^{19}$ is H, and $R^{11}$ is OH, $OR^A$, where $R^A$ is $C_{1-4}$ alkyl;
(b) $R^{19}$ and $R^{11}$ form a nitrogen-carbon double bond between the nitrogen and carbon atoms to which they are bound; or
(c) $R^{19}$ is H and $R^{11}$ is $SO_zM$, where z is 2 or 3 and M is a monovalent pharmaceutically acceptable cation;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;
$R^{6'}$, $R^{7'}$, $R^{9'}$ are selected from the same groups as $R^6$, $R^7$ and $R^9$ respectively and $R^{10'}$ and
$R^{11'}$ are the same as $R^{10}$ and $R^{11}$, wherein if $R^{11}$ and $R^{11'}$ are $SO_zM$, M may represent a divalent pharmaceutically acceptable cation.

A second aspect of the present invention provides the use of a compound of the first aspect of the invention in the manufacture of a medicament for treating a proliferative disease. The second aspect also provides a compound of the first aspect of the invention for use in the treatment of a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

A third aspect of the present invention comprises a compound of formula II:

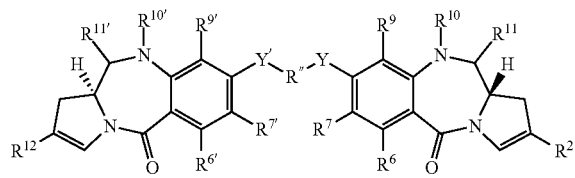

I wherein:
$R^2$ is of formula II.

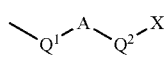

II where A is a $C_{5-7}$ aryl group, X is selected from the group comprising: OH, SH, $CO_2H$, COH, N=C=O, $NHR^N$, wherein $R^N$ is selected from the group comprising H and $C_{1-4}$ alkyl, and $(OC_2H_4)_mOCH_3$, where m is 1 to 3, and either:
(i) $Q^1$ is a single bond, and $Q^2$ is selected from a single bond and —Z—$(CH_2)_n$—, where Z is selected from a single bond, O, S and NH and is from 1 to 3; or
(ii) $Q^1$ is —CH=CH—, and $Q^2$ is a single bond;
$R^{12}$ is a $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NHRR', nitro, $Me_3Sn$ and halo; either:
(a) $R^{19}$ is carbamate nitrogen protecting group, and $R^{11}$ is O-Prot°, wherein Prot° is an oxygen protecting group;
(b) $R^{19}$ is a hemi-aminal nitrogen protecting group and $R^{11}$ is an oxo group; R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;
$R^{6'}$, $R^{7'}$, $R^{9'}$ are selected from the same groups as $R^6$, $R^7$ and $R^9$ respectively and $R^{10'}$ and $R^{11'}$ are the same as $R^{19}$ and $R^{11}$.

A fourth aspect of the present invention comprises a method of making a compound of formula I from a compound of formula II by deprotection of the imine bond.

The unsymmetrical dimeric PBD compounds of the present invention are made by different strategies to those previously employed in making symmetrical dimeric PBD compounds. In particular, the present inventors have developed a method which involves adding each each C2 aryl substituent to a symmetrical PBD dimer core in separate method steps. Accordingly, a fifth aspect of the present invention provides a method of making a compound of the first or third aspect of the invention, comprising at least one of the method steps set out below.

DEFINITIONS

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$.

Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to:
$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline (N2), cinnoline ($N_2$), phthalazine ($N_2$), naphthyridine ($N_2$), pteridine ($N_4$);
$C_{11}$ (with 2 fused rings) derived from benzodiazepine ($N_2$);
$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and,
$C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$)($OR^2$), wherein $R^1$ and $R^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR($OR^1$)($OR^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)($OR^1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $O_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $O_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

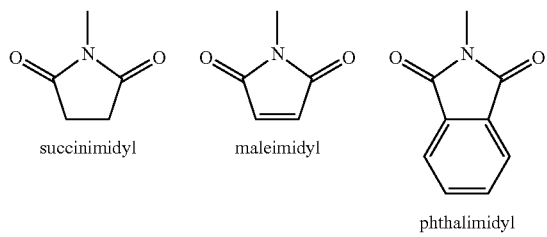

succinimidyl  maleimidyl  phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

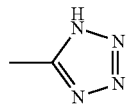

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.
Sulfonic acid (sulfo): —S(=O)$_2$OH, —SO$_3$H.
Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $O_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $O_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phosphor —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH—$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Oxygen protecting group: the term "oxygen protecting group" refers to a moiety which masks a hydroxy group, and these are well known in the art. A large number of suitable groups are described on pages 23 to 200 of Greene, T. W. and Wuts, G. M., Protective Groups in Organic Synthesis, 3$^{rd}$ Edition, John Wiley & Sons, Inc., 1999, which is incorporated herein by reference. Classes of particular interest include silyl ethers (e.g. TMS, TBDMS), substituted methyl ethers (e.g. THP) and esters (e.g. acetate).

Carbamate nitrogen protecting group: the term "carbamate nitrogen protecting group" pertains to a moiety which masks the nitrogen in the imine bond, and these are well known in the art. These groups have the following structure:

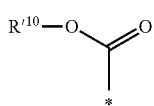

wherein R'¹⁰ is R as defined above. A large number of suitable groups are described on pages 503 to 549 of Greene, T. W. and Wuts, G. M., Protective Groups in Organic Synthesis, 3rd Edition, John Wiley & Sons, Inc., 1999, which is incorporated herein by reference.

Hemi-aminal nitrogen protecting group: the term "hemi-aminal nitrogen protecting group" pertains to a group having the following structure:

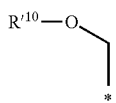

wherein R'¹⁰ is R as defined above. A large number of suitable groups are described on pages 633 to 647 as amide protecting groups of Greene, T. W. and Wuts, G. M., Protective Groups in Organic Synthesis, 3rd Edition, John Wiley & Sons, Inc., 1999, which is incorporated herein by reference.

Methods of Treatment

The compounds of the present invention may be used in a method of therapy. Also provided is a method of treatment, comprising administering to a subject in need of treatment a therapeutically-effective amount of a compound of formula I. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes Other Forms

Unless otherwise specified, included in the above are the well known ionic, salt, solvate, and protected forms of these substituents. For example, a reference to carboxylic acid (—COON) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COON may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e. NH₄⁺) and substituted ammonium ions (e.g. NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g. —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Carbinolamines

The invention includes compounds where a solvent adds across the imine bond of the PBD moiety, which is illustrated below where the solvent is water or an alcohol ($R^4OH$, where $R^4$ is $C_{1-4}$ alkyl):

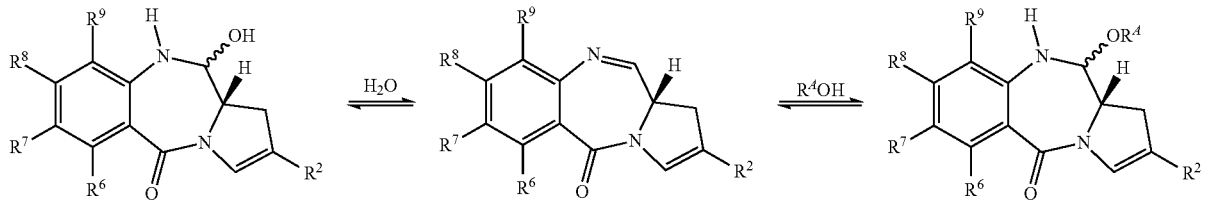

These forms can be called the carbinolamine and carbinolamine ether forms of the PBD. The balance of these equilibria depend on the conditions in which the compounds are found, as well as the nature of the moiety itself.

These particular compounds may be isolated in solid form, for example, by lyophilisation.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

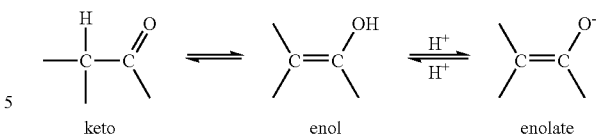

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

General Synthetic Routes

The synthesis of PBD compounds is extensively discussed in the following references, which discussions are incorporated herein by reference:

a) WO 00/12508 (pages 14 to 30);
b) WO 2005/023814 (pages 3 to 10);
c) WO 2004/043963 (pages 28 to 29); and
d) WO 2005/085251 (pages 30 to 39).

Synthesis Route

The compounds of the present invention, where $R^{10}$ and $R^{11}$ form a nitrogen-carbon double bond between the nitrogen and carbon atoms to which they are bound, can be synthesised from a compound of Formula 2:

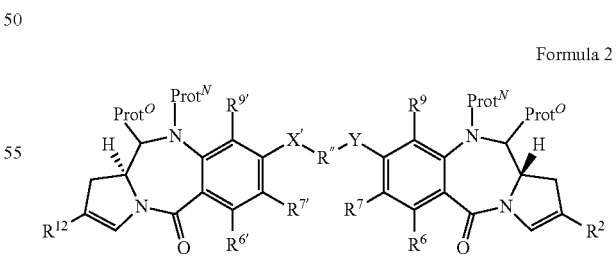

Formula 2 where $R^2$, $R^6$, $R^7$, $R^9$, $R^{6'}$, $R^{7'}$, $R^{9'}$, $R^{12}$, X, X' and R" are as defined for compounds of formula I, $Prot^N$ is a nitrogen protecting group for synthesis and $Prot^O$ is a protected oxygen group for synthesis or an oxo group, by deprotecting the imine bond by standard methods.

The compound produced may be in its carbinolamine or carbinolamine ether form depending on the solvents used. For example if Prot$^N$ is Alloc and Prot$^O$ is an oxygen protecting group for synthesis, then the deprotection is carried using palladium to remove the N10 protecting group, followed by the elimination of the oxygen protecting group for synthesis. If Prot$^N$ is Troc and Prot$^O$ is an oxygen protecting group for synthesis, then the deprotection is carried out using a Cd/Pb couple to yield the compound of formula (I). If Prot$^N$ is SEM, or an analogous group, and Prot$^O$ is an oxo group, then the oxo group can be removed by reduction, which leads to a protected carbinolamine intermediate, which can then be treated to remove the SEM protecting group, followed by the elimination of water. The reduction of the compound of Formula 2 can be accomplished by, for example, lithium tetraborohydride, whilst a suitable means for removing the SEM protecting group is treatment with silica gel.

Compounds of formula 2 can be synthesised from a compound of formula 3a:

Formula 3a

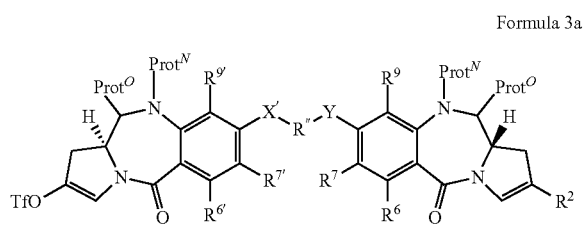

where $R^2$, $R^6$, $R^7$, $R^9$, $R^{6'}$, $R^{7'}$, $R^{9'}$, X, X' and R" are as defined for compounds of formula 2, by coupling an organometallic derivative comprising $R^{12}$, such as an organoboron derivative. The organoboron derivative may be a boronate or boronic acid.

Compounds of formula 2 can be synthesised from a compound of formula 3b:

Formula 3b

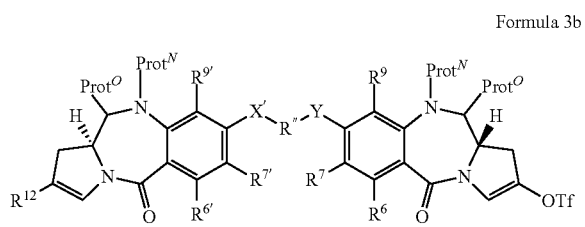

where $R^{12}$, $R^6$, $R^7$, $R^9$, $R^{6'}$, $R^{7'}$, $R^{9'}$, X, X' and R" are as defined for compounds of formula 2, by coupling an organometallic derivative comprising $R^2$, such as an organoboron derivative. The organoboron derivative may be a boronate or boronic acid.

Compounds of formulae 3a and 3b can be synthesised from a compound of formula 4:

Formula 4

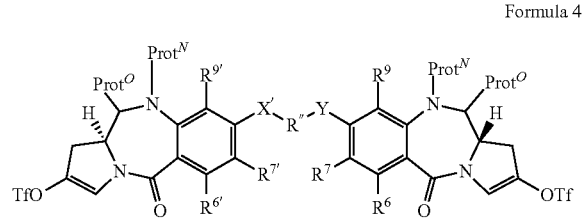

where $R^2$, $R^6$, $R^7$, $R^9$, $R^{6'}$, $R^{7'}$, $R^{9'}$, X, X' and R" are as defined for compounds of formula 2, by coupling about a single equivalent (e.g. 0.9 or 1 to 1.1 or 1.2) of an organometallic derivative, such as an organoboron derivative, comprising $R^2$ or $R^{12}$.

The couplings described above are usually carried out in the presence of a palladium catalyst, for example Pd(PPh$_3$)$_4$, Pd(OCOCH$_3$)$_2$, PdCl$_2$, Pd$_2$(dba)$_3$. The coupling may be carried out under standard conditions, or may also be carried out under microwave conditions.

The two coupling steps are usually carried out sequentially. They may be carried out with or without purification between the two steps. If no purification is carried out, then the two steps may be carried out in the same reaction vessel. Purification is usually required after the second coupling step. Purification of the compound from the undesired by-products may be carried out by column chromatography or ion-exchange separation.

The synthesis of compounds of formula 4 where Prot$^O$ is an oxo group and Prot$^N$ is SEM are described in detail in WO 00/12508, which is incorporated herein by reference. In particular, reference is made to scheme 7 on page 24, where the above compound is designated as intermediate P. This method of synthesis is also described in WO 2004/043963.

The synthesis of compounds of formula 4 where Prot$^O$ is a protected oxygen group for synthesis are described in WO 2005/085251, which synthesis is herein incorporated by reference.

Compounds of formula I where $R^{10}$ and $R^{10'}$ are H and $R^{11}$ and $R^{11'}$ are SON, can be synthesised from compounds of formula I where $R^{10}$ and $R^{11}$ form a nitrogen-carbon double bond between the nitrogen and carbon atoms to which they are bound, by the addition of the appropriate bisulphite salt or sulphinate salt, followed by an appropriate purification step. Further methods are described in GB 2 053 894, which is herein incorporated by reference.

Nitrogen Protecting Groups for Synthesis

Nitrogen protecting groups for synthesis are well known in the art. In the present invention, the protecting groups of particular interest are carbamate nitrogen protecting groups and hemi-aminal nitrogen protecting groups.

Carbamate nitrogen protecting groups have the following structure:

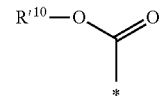

wherein $R'^{10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Particularly preferred protecting groups include Troc, Teoc, Fmoc, BOC, Doc, Hoc, TcBOC, 1-Adoc and 2-Adoc.

Other possible groups are nitrobenzyloxycarbonyl (e.g. 4-nitrobenzyloxycarbonyl) and 2-(phenylsulphonyl)ethoxycarbonyl.

Those protecting groups which can be removed with palladium catalysis are not preferred, e.g. Alloc.

Hemi-aminal nitrogen protecting groups have the following structure:

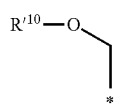

wherein R'¹⁰ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference. The groups disclosed herein can be applied to compounds of the present invention. Such groups include, but are not limited to, SEM, MOM, MTM, MEM, BOM, nitro or methoxy substituted BOM, Cl$_3$CCH$_2$OCH$_2$—.

Protected Oxygen Group for Synthesis

Protected oxygen group for synthesis are well known in the art. A large number of suitable oxygen protecting groups are described on pages 23 to 200 of Greene, T. W. and Wuts, G. M., Protective Groups in Organic Synthesis, 3$^{rd}$ Edition, John Wiley & Sons, Inc., 1999, which is incorporated herein by reference.

Classes of particular interest include silyl ethers, methyl ethers, alkyl ethers, benzyl ethers, esters, acetates, benzoates, carbonates, and sulfonates.

Preferred oxygen protecting groups include acetates, TBS and THP.

Further Preferences

The following preferences may apply to all aspects of the invention as described above, or may relate to a single aspect. The preferences may be combined together in any combination.

In some embodiments, $R^{6'}$, $R^{7'}$, $R^{9'}$, $R^{10'}$, $R^{11'}$ and Y' are preferably the same as $R^6$, $R^7$, $R^9$, $R^{10}$, $R^{11}$ and Y respectively.

Dimer Link

Y and Y' are preferably O.

R" is preferably a $C_{3-7}$ alkylene group with no substituents. More preferably R" is a $C_3$, $C_5$ or $C_7$ alkylene.

$R^6$ to $R^9$ $R^9$ is preferably H.

$R^6$ is preferably selected from H, OH, OR, SH, NH$_2$, nitro and halo, and is more preferably H or halo, and most preferably is H.

$R^7$ is preferably selected from H, OH, OR, SH, SR, NH$_2$, NHR, NRR', and halo, and more preferably independently selected from H, OH and OR, where R is preferably selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and OCH$_2$Ph.

These preferences apply to $R^{9'}$, $R^{6'}$ and $R^{7'}$ respectively.

$R^2$

A in $R^2$ may be phenyl group or a $C_{5-7}$ heteroaryl group, for example furanyl, thiophenyl and pyridyl. In some embodiments, A is preferably phenyl. In other embodiments, A is preferably thiophenyl, for example, thiophen-2-yl and thiophen-3-yl.

X is a group selected from the list comprising: OH, SH, CO$_2$H, COH, N=C=O and NHR$^N$, wherein R$^N$ is selected from the group comprising H and $C_{1-4}$ alkyl. X may preferably be: OH, SH, CO$_2$H, —N=C=O or NH$_2$, and may more preferably be: OH, SH, or NH$_2$, and most preferably is NH$_2$.

Q$^2$-X may be on any of the available ring atoms of the $C_{5-7}$ aryl group, but is preferably on a ring atom that is not adjacent the bond to the remainder of the compound, i.e. it is preferably β or γ to the bond to the remainder of the compound. Therefore, where the $C_{5-7}$ aryl group (A) is phenyl, the substituent (Q$^2$-X) is preferably in the meta- or para-positions, and more preferably is in the para-position.1

In some embodiments, Q$^1$ is a single bond. In these embodiments, Q$^2$ is selected from a single bond and —Z—(CH$_2$)$_n$—, where Z is selected from a single bond, O, S and NH and is from 1 to 3. In some of these embodiments, Q$^2$ is a single bond. In other embodiments, Q$^2$ is —Z—(CH$_2$)$_n$—. In these embodiments, Z may be O or S and n may be 1 or n may be 2. In other of these embodiments, Z may be a single bond and n may be 1.

In other embodiments, Q$^1$ is —CH=CH—.

In some embodiments, R$^2$ may be -A-CH$_2$—X and -A-X. In these embodiments, X may be OH, SH, CO$_2$H, COH and NH$_2$. In particularly preferred embodiments, X may be NH$_2$.

$R^{12}$ $R^{12}$ may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^{12}$ is preferably phenyl. In other embodiments, $R^{12}$ is preferably thiophenyl, for example, thiophen-2-yl and thiophen-3-yl.

$R^{12}$ may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4-yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4-yl, isoquinolin-5-yl, isoquinolin-6-yl, isoquinolin-7-yl and isoquinolin-8-yl. Of these isoquinolin-3-yl and isoquinolin-6-yl may be preferred.

$R^{12}$ may bear any number of substituent groups. It preferably bears from 1 to 3 substituent groups, with 1 and 2 being more preferred, and singly substituted groups being most preferred. The substituents may be any position.

Where $R^{12}$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^{12}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^{12}$ Substituents

If a substituent on $R^{12}$ is halo, it is preferably F or Cl, more preferably Cl.

If a substituent on $R^{12}$ is ether, it may in some embodiments be an alkoxy group, for example, a $C_{1-7}$ alkoxy group (e.g. methoxy, ethoxy) or it may in some embodiments be a $C_{5-7}$ aryloxy group (e.g. phenoxy, pyridyloxy, furanyloxy). The alkoxy group may itself be further substituted, for example by an amino group (e.g. dimethylamino).

If a substituent on $R^{12}$ is $C_{1-7}$ alkyl, it may preferably be a $C_{1-4}$ alkyl group (e.g. methyl, ethyl, propryl, butyl).

If a substituent on $R^{12}$ is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^{12}$ is bis-oxy-$C_{1-3}$ alkylene, this is preferably bis-oxy-methylene or bis-oxy-ethylene.

Particularly preferred substituents for $R^{12}$ include methoxy, ethoxy, fluoro, chloro, cyano, bis-oxy-methylene, methyl-piperazinyl, morpholino and methyl-thiophenyl. Another particularly preferred substituent for $R^{12}$ is dimethylaminopropyloxy.

$R^{12}$ Groups

Particularly preferred substituted $R^{12}$ groups include, but are not limited to, 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl.

M and z

It is preferred that M and M' are monovalent pharmaceutically acceptable cations, and are more preferably $Na^+$.

z is preferably 3.

$3^{rd}$ Aspect

The preferences expressed above for the first aspect may apply to the compounds of this aspect, where appropriate.

When $R^{13}$ is carbamate nitrogen protecting group, it may preferably be Teoc, Fmoc and Troc, and may more preferably be Troc.

When $R^{11}$ is O-$Prot^O$, wherein $Prot^O$ is an oxygen protecting group, $Prot^O$ may preferably be TBS or THP, and may more preferably be TBS.

When $R^{10}$ is a hemi-aminal nitrogen protecting group, it may preferably be MOM, BOM or SEM, and may more preferably be SEM.

EXAMPLES

General Experimental Methods

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1H$ and $^{13}C$ NMR spectra were acquired at 300 K using a Bruker Avance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

Compound 1b was synthesised as described in WO 00/012508 (compound 210), which is herein incorporated by reference.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm LC/MS conditions specific for compounds protected by both a Troc and a TBDMs group: Chromatographic separation of Troc and TBDMS protected compounds was performed on a Waters Alliance 2695 HPLC system utilizing a Onyx Monolitic reversed-phase column (3 μm particles, 50×4.6 mm) from Phenomenex Corp. Mobile-phase A consisted of 5% acetonitrile—95% water containing 0.1% formic acid, and mobile phase B consisted of 95% acetonitrile—5% water containing 0.1% formic acid. After 1 min at 5% B, the proportion of B was raised to 95% B over the next 2.5 min and maintained at 95% B for a further 1 min, before returning to 95% A in 10 s and re-equilibration for a further 50 sec, giving a total run time of 5.0 min. The flow rate was maintained at 3.0 mL/min.

LC/MS conditions specific for compound 33: LC was run on a Waters 2767 sample Manager coupled with a Waters 2996 photodiode array detector and a Waters ZQ single quadruple mass Spectrometer. The column used was Luna Phenyl-Hexyl 150×4.60 mm, 5 μm, Part no. 00E-4257-E0 (Phenomenex). The mobile phases employed were:

Mobile phase A: 100% of HPLC grade water (0.05% triethylamine), pH=7

Mobile phase B: 20% of HPLC grade water and 80% of HPLC grade acetonitrile (0.05% triethylamine), pH=7

The gradients used were:

| Time (min) | Flow Rate (ml/min) | % A | % B |
|---|---|---|---|
| Initial | 1.50 | 90 | 10 |
| 1.0 | 1.50 | 90 | 10 |
| 16.0 | 1.50 | 64 | 36 |
| 30.0 | 1.50 | 5 | 95 |
| 31.0 | 1.50 | 90 | 10 |
| 32.0 | 1.50 | 90 | 10 |

Mass Spectrometry was carried out in positive ion mode and SIR (selective ion monitor) and the ion monitored was m/z=727.2.

Synthesis of Key Intermediates
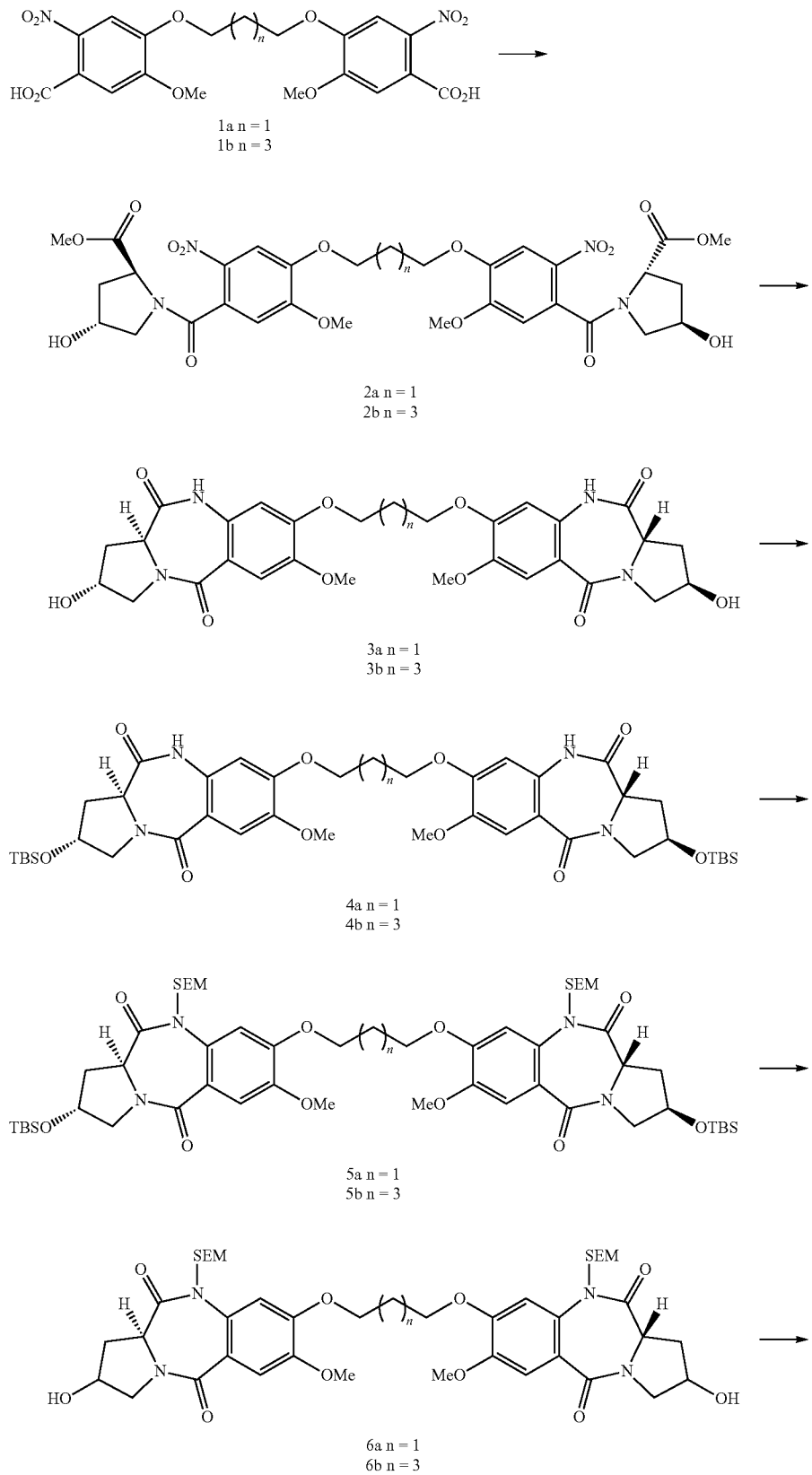

-continued

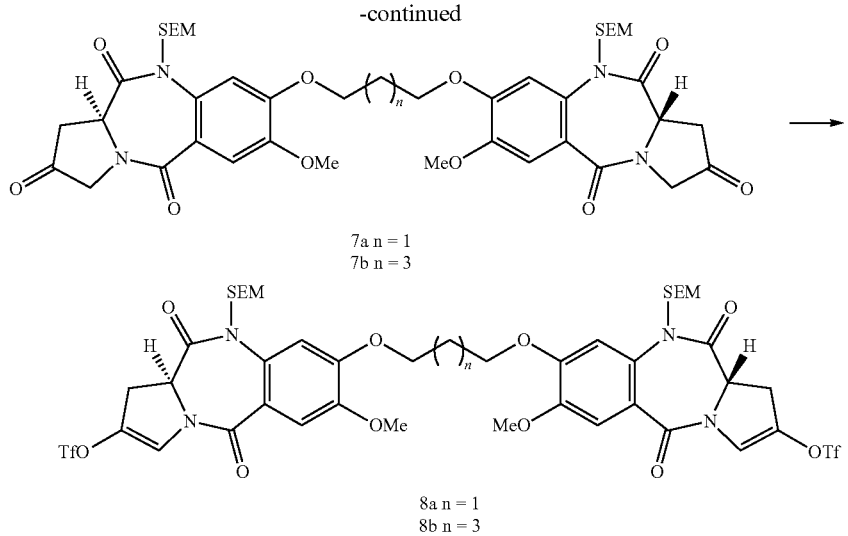

7a n = 1
7b n = 3

8a n = 1
8b n = 3

(a) 1,1'-[[(Propane-1,3-diyl)dioxy]bis[(5-methoxy-2-nitro-1,4-phenylene)carbonyl]]bis[(2S,4R)-methyl-4-hydroxypyrrolidine-2-carboxylate] (2a)

Method A:

A catalytic amount of DMF (2 drops) was added to a stirred solution of the nitro-acid 1a (1.0 g, 2.15 mmol) and oxalyl chloride (0.95 mL, 1.36 g, 10.7 mmol) in dry THF (20 mL). The reaction mixture was allowed to stir for 16 hours at room temperature and the solvent was removed by evaporation in vacuo. The resulting residue was re-dissolved in dry THF (20 mL) and the acid chloride solution was added dropwise to a stirred mixture of (2S,4R)-methyl-4-hydroxypyrrolidine-2-carboxylate hydrochloride (859 mg, 4.73 mmol) and TEA (6.6 mL, 4.79 g, 47.3 mmol) in THF (10 mL) at −30° C. (dry ice/ethylene glycol) under a nitrogen atmosphere. The reaction mixture was allowed to warm to room temperature and stirred for a further 3 hours after which time TLC (95:5 v/v $CHCl_3$/MeOH) and LC/MS (2.45 min (ES+) m/z (relative intensity) 721 ([M+H]$^+$, 20)) revealed formation of product. Excess THF was removed by rotary evaporation and the resulting residue was dissolved in DCM (50 mL). The organic layer was washed with 1N HCl (2×15 mL), saturated $NaHCO_3$ (2×15 mL), $H_2O$ (20 mL), brine (30 mL) and dried ($MgSO_4$). Filtration and evaporation of the solvent gave the crude product as a dark coloured oil. Purification by flash chromatography (gradient elution: 100% $CHCl_3$ to 96:4 v/v $CHCl_3$/MeOH) isolated the pure amide 2a as an orange coloured glass (840 mg, 54%).

Method B:

Oxalyl chloride (9.75 mL, 14.2 g, 111 mmol) was added to a stirred suspension of the nitro-acid 1a (17.3 g, 37.1 mmol) and DMF (2 mL) in anhydrous DCM (200 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation in vacuo, the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 minutes to a stirred suspension of (2S,4R)-methyl-4-hydroxypyrrolidine-2-carboxylate hydrochloride (15.2 g, 84.0 mmol) and TEA (25.7 mL, 18.7 g, 185 mmol) in DCM (150 mL) at −40° C. (dry ice/$CH_3CN$). Immediately, the reaction was complete as judged by LC/MS (2.47 min (ES+) m/z (relative intensity) 721 ([M+H]$^+$, 100)). The mixture was diluted with DCM (150 mL) and washed with 1N HCl (300 mL), saturated $NaHCO_3$ (300 mL), brine (300 mL), filtered (through a phase separator) and the solvent evaporated in vacuo to give the pure product 2a as an orange solid (21.8 g, 82%).

Analytical Data:

$[\alpha]^{22}_D$=−46.1° (c=0.47, $CHCl_3$); $^1$H NMR (400 MHz, $CDCl_3$) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); $^{13}$C NMR (100 MHz, $CDCl_3$) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, $CHCl_3$) 3410 (br), 3010, 2953, 1741, 1622, 1577, 1519, 1455, 1429, 1334, 1274, 1211, 1177, 1072, 1050, 1008, 871 cm$^{-1}$; MS (ES$^+$) m/z (relative intensity) 721 ([M+H]$^{+\cdot}$, 47), 388 (80); HRMS [M+H]$^{+\cdot}$ theoretical $C_{31}H_{36}N_4O_{16}$ m/z 721.2199. found (ES$^+$) m/z 721.2227.

(a) 1,1'-[[(Pentane-1,5-diyl)dioxy]bis[(5-methoxy-2-nitro-1,4-phenylene)carbonyl]]bis[(2S,4R)-methyl-4-hydroxypyrrolidine-2-carboxylate] (2b)

Preparation from 1b according to Method B gave the pure product as an orange foam (75.5 g, 82%).

Analytical Data:

(ES$^+$) m/z (relative intensity) 749 ([M+H]$^{+\cdot}$, 100).

(b) 1,1'-[[(Propane-1,3-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione] (3a)

Method A:

A suspension of 10% Pd/C (7.5 g, 10% w/w) in DMF (40 mL) was added to a solution of the nitro-ester 2a (75 g, 104 mmol) in DMF (360 mL). The suspension was hydrogenated in a Parr hydrogenation apparatus over 8 hours. Progress of the reaction was monitored by LC/MS (2.12 min (ES+) m/z (relative intensity) 597 ([M+H]$^{+\cdot}$, 100), (ES−) m/z (relative intensity) 595 ([M+H]$^{+\cdot}$, 100) after the hydrogen uptake had stopped. Solid Pd/C was removed by filtration and the filtrate was concentrated by rotary evaporation under vacuum (below 10 mbar) at 40° C. to afford a dark oil containing traces of DMF and residual charcoal. The residue was digested in EtOH (500 mL) at 40° C. on a water bath (rotary evaporator bath) and the resulting suspension was filtered through celite and washed with ethanol (500 mL) to give a clear filtrate. Hydrazine hydrate (10 mL, 321 mmol) was added to the solution and the reaction mixture was heated at reflux. After 20 minutes the formation of a white precipitate was observed and reflux was allowed to continue for a further 30 minutes. The mixture was allowed to cool down to room temperature and the precipitate was retrieved by filtration, washed with diethyl ether (2*1 volume of precipitate) and dried in a vacuum desiccator to provide 3a (50 g, 81%).

Method B:

A solution of the nitro-ester 2a (6.80 g, 9.44 mmol) in MeOH (300 mL) was added to Raney™ nickel (4 large spatula ends of a ~50% slurry in H$_2$O) and anti-bumping granules in a 3-neck round bottomed flask. The mixture was heated at reflux and then treated dropwise with a solution of hydrazine hydrate (5.88 mL, 6.05 g, 188 mmol) in MeOH (50 mL) at which point vigorous effervescence was observed. When the addition was complete (~30 minutes) additional Raney™ nickel was added carefully until effervescence had ceased and the initial yellow colour of the reaction mixture was discharged. The mixture was heated at reflux for a further 30 minutes at which point the reaction was deemed complete by TLC (90:10 v/v CHCl$_3$/MeOH) and LC/MS (2.12 min (ES+) m/z (relative intensity) 597 ([M+H]$^{+\cdot}$, 100)). The reaction mixture was allowed to cool to around 40° C. and then excess nickel removed by filtration through a sinter funnel without vacuum suction. The filtrate was reduced in volume by evaporation in vacuo at which point a colourless precipitate formed which was collected by filtration and dried in a vacuum desiccator to provide 3a (5.40 g, 96%).

Analytical Data:

$[\alpha]^{27}_D$=+404° (c=0.10, DMF); $^1$H NMR (400 MHz, DMSO-d$_6$) δ 10.2 (s, 2H, NH), 7.26 (s, 2H), 6.73 (s, 2H), 5.11 (d, 2H, J=3.98 Hz, OH), 4.32-4.27 (m, 2H), 4.19-4.07 (m, 6H), 3.78 (s, 6H), 3.62 (dd, 2H, J=12.1, 3.60 Hz), 3.43 (dd, 2H, J=12.0, 4.72 Hz), 2.67-2.57 (m, 2H), 2.26 (p, 2H, J=5.90 Hz), 1.99-1.89 (m, 2H); $^{13}$C NMR (100 MHz, DMSO-d$_6$) δ 169.1, 164.0, 149.9, 144.5, 129.8, 117.1, 111.3, 104.5, 54.8, 54.4, 53.1, 33.5, 27.5; IR (ATR, neat) 3438, 1680, 1654, 1610, 1605, 1516, 1490, 1434, 1379, 1263, 1234, 1216, 1177, 1156, 1115, 1089, 1038, 1018, 952, 870 cm$^{-1}$; MS (ES$^+$) m/z (relative intensity) 619 ([M+Na]$^{+\cdot}$, 10), 597 ([M+H]$^{+\cdot}$, 52), 445 (12), 326 (11); HRMS [M+H]$^{+\cdot}$ theoretical C$_{29}$H$_{32}$N$_4$O$_{10}$ m/z 597.2191. found (ES$^+$) m/z 597.2205.

(b) 1,1'-[[(Pentane-1,5-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione] (3b)

Preparation from 2b according to Method A gave the product as a white solid (22.1 g, 86%).

Analytical Data:

MS (ES$^-$) m/z (relative intensity) 623.3 ([M−H]$^-$, 100);

(c) 1,1'-[[(Propane-1,3-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione] (4a)

TBSCl (317 mg, 2.1 mmol) and imidazole (342 mg, 5.03 mmol) were added to a cloudy solution of the tetralactam 3a (250 mg, 0.42 mmol) in anhydrous DMF (6 mL). The mixture was allowed to stir under a nitrogen atmosphere for 3 hours after which time the reaction was deemed complete as judged by LC/MS (3.90 min (ES+) m/z (relative intensity) 825 ([M+H]$^{+\cdot}$, 100)). The reaction mixture was poured onto ice (~25 mL) and allowed to warm to room temperature with stirring. The resulting white precipitate was collected by vacuum filtration, washed with H$_2$O, diethyl ether and dried in the vacuum desiccator to provide pure 4a (252 mg, 73%).

Analytical Data:

$[\alpha]^{23}_D$=+234° (c=0.41, CHCl$_3$); $^1$H NMR (400 MHz, CDCl$_3$) δ 8.65 (s, 2H, NH), 7.44 (s, 2H), 6.54 (s, 2H), 4.50 (p, 2H, J=5.38 Hz), 4.21-4.10 (m, 6H), 3.87 (s, 6H), 3.73-3.63 (m, 4H), 2.85-2.79 (m, 2H), 2.36-2.29 (m, 2H), 2.07-1.99 (m, 2H), 0.86 (s, 18H), 0.08 (s, 12H); $^{13}$C NMR (100 MHz, CDCl$_3$) δ 170.4, 165.7, 151.4, 146.6, 129.7, 118.9, 112.8, 105.3, 69.2, 65.4, 56.3, 55.7, 54.2, 35.2, 28.7, 25.7, 18.0, −4.82 and −4.86; IR (ATR, CHCl$_3$) 3235, 2955, 2926, 2855, 1698, 1695, 1603, 1518, 1491, 1446, 1380, 1356, 1251, 1220, 1120, 1099, 1033 cm$^{-1}$; MS (ES$^+$) m/z (relative intensity) 825 ([M+H]$^{+\cdot}$, 62), 721 (14), 440 (38); HRMS [M+H]$^{+\cdot}$ theoretical C$_{41}$H$_{60}$N$_4$O$_{10}$Si$_2$ m/z 825.3921. found (ES$^+$) m/z 825.3948.

(c) 1,1'-[[(Pentane-1,5-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione] (4b)

Preparation from 3b according to the above method gave the product as a white solid (27.3 g, 93%).

Analytical Data:

MS (ES$^+$) m/z (relative intensity) 853.8 ([M+H]$^{+\cdot}$, 100), (ES$^-$) m/z (relative intensity) 851.6 ([M−H]$^-$, 100.

(d) 1,1'-[[(Propane-1,3-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (5a)

A solution of n-BuLi (4.17 mL of a 1.6 M solution in hexane, 6.67 mmol) in anhydrous THF (10 mL) was added dropwise to a stirred suspension of the tetralactam 4a (2.20 g, 2.67 mmol) in anhydrous THF (30 mL) at −30° C. (dry ice/ethylene glycol) under a nitrogen atmosphere. The reaction mixture was allowed to stir at this temperature for 1 hour (now a reddish orange colour) at which point a solution of SEMCl (1.18 mL, 1.11 g, 6.67 mmol) in anhydrous THF (10 mL) was added dropwise. The reaction mixture was allowed to slowly warm to room temperature and was stirred for 16 hours under a nitrogen atmosphere. The reaction was deemed complete as judged by TLC (EtOAc) and LC/MS (4.77 min (ES+) m/z (relative intensity) 1085 ([M+H]$^{+\cdot}$, 100)). The THF was removed by evaporation in vacuo and the resulting residue dissolved in EtOAc (60 mL), washed with H$_2$O (20 mL), brine (20 mL), dried (MgSO$_4$) filtered and evaporated in vacuo to provide the crude product. Purification by flash chromatography (80:20 v/v Hexane/EtOAc) gave the pure N10-SEM-protected tetralactam 5a as an oil (2.37 g, 82%).

Analytical Data:

$[\alpha]^{23}_D$=+163° (c=0.41, CHCl$_3$); $^1$H NMR (400 MHz, CDCl$_3$) δ 7.33 (s, 2H), 7.22 (s, 2H), 5.47 (d, 2H, J=9.98 Hz), 4.68 (d, 2H, J=9.99 Hz), 4.57 (p, 2H, J=5.77 Hz), 4.29-4.19 (m, 6H), 3.89 (s, 6H), 3.79-3.51 (m, 8H), 2.87-2.81 (m, 2H), 2.41 (p, 2H, J=5.81 Hz), 2.03-1.90 (m, 2H), 1.02-0.81 (m, 22H), 0.09 (s, 12H), 0.01 (s, 18H); $^{13}$C NMR (100 MHz, CDCl$_3$) δ 170.0, 165.7, 151.2, 147.5, 133.8, 121.8, 111.6, 106.9, 78.1, 69.6, 67.1, 65.5, 56.6, 56.3, 53.7, 35.6, 30.0, 25.8, 18.4, 18.1, −1.24, −4.73; IR (ATR, CHCl$_3$) 2951, 1685, 1640, 1606, 1517, 1462, 1433, 1360, 1247, 1127, 1065 cm$^{-1}$; MS (ES$^+$) m/z (relative intensity) 1113 ([M+Na]$^{+\cdot}$, 48), 1085 ([M+H]$^{+\cdot}$, 100), 1009 (5), 813 (6); HRMS [M+H]$^{+\cdot}$ theoretical C$_{53}$H$_{88}$N$_4$O$_{12}$Si$_4$ m/z 1085.5548. found (ES$^+$) m/z 1085.5542.

(d) 1,1'-[[(Pentane-1,5-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (5b)

Preparation from 4b according to the above method gave the product as a pale orange foam (46.9 g, 100%), used without further purification.

Analytical Data:

MS (ES$^+$) m/z (relative intensity) 1114 ([M+H]$^{+\cdot}$, 90), (ES) m/z (relative intensity) 1158 ([M+2Na]$^{-\cdot}$, 100).

(e) 1,1'-[[(Propane-1,3-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (6a)

A solution of TBAF (5.24 mL of a 1.0 M solution in THF, 5.24 mmol) was added to a stirred solution of the bis-silyl ether 5a (2.58 g, 2.38 mmol) in THF (40 mL) at room temperature. After stirring for 3.5 hours, analysis of the reaction mixture by TLC (95:5 v/v CHCl$_3$/MeOH) revealed completion of reaction. The reaction mixture was poured into a solution of saturated NH$_4$Cl (100 mL) and extracted with EtOAc (3×30 mL). The combined organic layers were washed with brine (60 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave the pure tetralactam 6a as a white foam (1.78 g, 87%).

Analytical Data:

$[\alpha]^{23}_D$=+202° (c=0.34, CHCl$_3$); $^1$H NMR (400 MHz, CDCl$_3$) δ 7.28 (s, 2H), 7.20 (s, 2H), 5.44 (d, 2H, J=10.0 Hz), 4.72 (d, 2H, J=10.0 Hz), 4.61-4.58 (m, 2H), 4.25 (t, 4H, J=5.83 Hz), 4.20-4.16 (m, 2H), 3.91-3.85 (m, 8H), 3.77-3.54 (m, 6H), 3.01 (br s, 2H, OH), 2.96-2.90 (m, 2H), 2.38 (p, 2H, J=5.77 Hz), 2.11-2.05 (m, 2H), 1.00-0.91 (m, 4H), 0.00 (s, 18H); $^{13}$C NMR (100 MHz, CDCl$_3$) δ 169.5, 165.9, 151.3, 147.4, 133.7, 121.5, 111.6, 106.9, 79.4, 69.3, 67.2, 65.2, 56.5, 56.2, 54.1, 35.2, 29.1, 18.4, −1.23; IR (ATR, CHCl$_3$) 2956, 1684, 1625, 1604, 1518, 1464, 1434, 1361, 1238, 1058, 1021 cm$^{-1}$; MS (ES$^+$) m/z (relative intensity) 885 ([M+29]$^{+\cdot}$, 70), 857 ([M+H]$^{+\cdot}$, 100), 711 (8), 448 (17); HRMS [M+H]$^{+\cdot}$ theoretical C$_{41}$H$_{60}$N$_4$O$_{12}$Si$_2$ m/z 857.3819. found (ES$^+$) m/z 857.3826.

(e) 1,1'-[[(Pentane-1,5-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (6b)

Preparation from 5b according to the above method gave the product as a white foam (15.02 g).

Analytical Data:

MS (ES$^+$) m/z (relative intensity) 886 ([M+H]$^{+\cdot}$, 10), 739.6 (100), (ES$^-$) m/z (relative intensity) 884 ([M−H]$^{-\cdot}$, 40).

(f) 1,1'-[[(Propane-1,3-diyl)dioxy]bis[(11aS)-11-sulpho-7-methoxy-2-oxo-10-((2-(trimethylsilyl)ethoxy)methyl)1,2,3,10,11,11a-hexahydro-5H-pyrrolo[2,1-c][1,4]benzodiazepin-5,11-dione]] (7a)

Method A:

A 0.37 M sodium hypochlorite solution (142.5 mL, 52.71 mmol, 2.4 eq) was added dropwise to a vigorously stirred mixture of the diol 6a (18.8 g, 21.96 mmol, 1 eq), TEMPO (0.069 g, 0.44 mmol, 0.02 eq) and 0.5 M potassium bromide solution (8.9 mL, 4.4 mmol, 0.2 eq) in DCM (115 mL) at 0° C. The temperature was maintained between 0° C. and 5° C. by adjusting the rate of addition. The resultant yellow emulsion was stirred at 0° C. to 5° C. for 1 hour. TLC (EtOAc) and LC/MS [3.53 min. (ES+) m/z (relative intensity) 875 ([M+Na]$^{+\cdot}$, 50), (ES−) m/z (relative intensity) 852 ([M−H]$^{-\cdot}$, 100)] indicated that reaction was complete.

The reaction mixture was filtered, the organic layer separated and the aqueous layer was backwashed with DCM (×2). The combined organic portions were washed with brine (×1), dried (MgSO$_4$) and evaporated to give a yellow foam. Purification by flash column chromatography (gradient elution 35/65 v/v n-hexane/EtOAC, 30/70 to 25/75 v/v n-hexane/EtOAC) afforded the bis-ketone 7a as a white foam (14.1 g, 75%).

Sodium hypochlorite solution, reagent grade, available at chlorine 10-13%, was used. This was assumed to be 10% (10 g NaClO in 100 g) and calculated to be 1.34 M in NaClO. A stock solution was prepared from this by diluting it to 0.37 M with water. This gave a solution of approximately pH 14. The pH was adjusted to 9.3 to 9.4 by the addition of solid NaHCO$_3$. An aliquot of this stock was then used so as to give 2.4 mol eq. for the reaction.

On addition of the bleach solution an initial increase in temperature was observed. The rate of addition was controlled, to maintain the temperature between 0° C. to 5° C. The reaction mixture formed a thick, lemon yellow coloured, emulsion.

The oxidation was an adaptation of the procedure described in Thomas Fey et al, J. Org. Chem., 2001, 66, 8154-8159.

Method B:

Solid TCCA (10.6 g, 45.6 mmol) was added portionwise to a stirred solution of the alcohol 6a (18.05 g, 21.1 mmol) and TEMPO (123 mg, 0.78 mmol) in anhydrous DCM (700 mL) at 0° C. (ice/acetone). The reaction mixture was stirred at 0° C. under a nitrogen atmosphere for 15 minutes after which time TLC (EtOAc) and LC/MS [3.57 min (ES+) m/z (relative intensity) 875 ([M+Na]$^{+\cdot}$, 50)] revealed completion of reaction. The reaction mixture was filtered through celite and the filtrate was washed with saturated aqueous NaHCO$_3$ (400 mL), brine (400 mL), dried (MgSO$_4$), filtered and evaporated in vacuo to provide the crude product. Purification by flash column chromatography (80:20 v/v EtOAc/Hexane) afforded the bis-ketone 7a as a foam (11.7 g, 65%).

Method C:

A solution of anhydrous DMSO (0.72 mL, 0.84 g, 10.5 mmol) in dry DCM (18 mL) was added dropwise over a period of 25 min to a stirred solution of oxalyl chloride (2.63 mL of a 2.0 M solution in DCM, 5.26 mmol) under a nitrogen atmosphere at −60° C. (liq $N_2$/CHCl$_3$). After stirring at −55° C. for 20 minutes, a slurry of the substrate 6a (1.5 g, 1.75 mmol) in dry DCM (36 mL) was added dropwise over a period of 30 min to the reaction mixture. After stirring for a further 50 minutes at −55° C., a solution of TEA (3.42 mL, 2.49 g; 24.6 mmol) in dry DCM (18 mL) was added dropwise over a period of 20 min to the reaction mixture. The stirred reaction mixture was allowed to warm to room temperature (~1.5 h) and then diluted with DCM (50 mL). The organic solution was washed with 1 N HCl (2×25 mL), $H_2O$ (30 mL), brine (30 mL) and dried (MgSO$_4$). Filtration and evaporation of the solvent in vacuo afforded the crude product which was purified by flash column chromatography (80:20 v/v EtOAc/Hexane) to afford bis-ketone 7a as a foam (835 mg, 56%)

Analytical Data:

$[\alpha]^{20}_D$=+291° (c=0.26, CHCl$_3$); $^1$H NMR (400 MHz, CDCl$_3$) δ 7.32 (s, 2H), 7.25 (s, 2H), 5.50 (d, 2H, J=10.1 Hz), 4.75 (d, 2H, J=10.1 Hz), 4.60 (dd, 2H, J=9.85, 3.07 Hz), 4.31-4.18 (m, 6H), 3.89-3.84 (m, 8H), 3.78-3.62 (m, 4H), 3.55 (dd, 2H, J=19.2, 2.85 Hz), 2.76 (dd, 2H, J=19.2, 9.90 Hz), 2.42 (p, 2H, J=5.77 Hz), 0.98-0.91 (m, 4H), 0.00 (s, 18H); $^{13}$C NMR (100 MHz, CDCl$_3$) δ 206.8, 168.8, 165.9, 151.8, 148.0, 133.9, 120.9, 111.6, 107.2, 78.2, 67.3, 65.6, 56.3, 54.9, 52.4, 37.4, 29.0, 18.4, −1.24; IR (ATR, CHCl$_3$) 2957, 1763, 1685, 1644, 1606, 1516, 1457, 1434, 1360, 1247, 1209, 1098, 1066, 1023 cm$^{-1}$; MS (ES$^+$) m/z (relative intensity) 881 ([M+29]$^+$·, 38), 853 ([M+H]$^+$·, 100), 707 (8), 542 (12); HRMS [M+H]$^+$· theoretical $C_{41}H_{56}N_4O_{12}Si_2$ m/z 853.3506. found (ES$^+$) m/z 853.3502.

(f) 1,1'-[[(Pentane-1,5-diyl)dioxy]bis[(11aS)-11-sulpho-7-methoxy-2-oxo-10-((2-(trimethylsilyl)ethoxy)methyl)1,2,3,10,11,11a-hexahydro-5H-pyrrolo[2,1-c][1,4]benzodiazepin-5,11-dione]] (7b)

Preparation from 6b according to Method C gave the product as a white foam (10.5 g, 76%).

Analytical Data: MS (ES$^+$) m/z (relative intensity) 882 ([M+H]$^+$·, 30), 735 (100), (ES$^-$) m/z (relative intensity) 925 ([M+45]$^-$·, 100), 880 ([M−H]$^-$·, 70).

(g) 1,1'-[[(Propane-1,3-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (8a)

Anhydrous 2,6-lutidine (5.15 mL, 4.74 g, 44.2 mmol) was injected in one portion to a vigorously stirred solution of bis-ketone 7a (6.08 g, 7.1 mmol) in dry DCM (180 mL) at −45° C. (dry ice/acetonitrile cooling bath) under a nitrogen atmosphere. Anhydrous triflic anhydride, taken from a freshly opened ampoule (7.2 mL, 12.08 g, 42.8 mmol), was injected rapidly dropwise, while maintaining the temperature at −40° C. or below. The reaction mixture was allowed to stir at −45° C. for 1 hour at which point TLC (50/50 v/v n-hexane/EtOAc) revealed the complete consumption of starting material. The cold reaction mixture was immediately diluted with DCM (200 mL) and, with vigorous shaking, washed with water (1×100 mL), 5% citric acid solution (1×200 mL) saturated NaHCO$_3$ (200 mL), brine (100 mL) and dried (MgSO$_4$). Filtration and evaporation of the solvent in vacuo afforded the crude product which was purified by flash column chromatography (gradient elution: 90:10 v/v n-hexane/EtOAc to 70:30 v/v n-hexane/EtOAc) to afford bis-enol triflate 8a as a yellow foam (5.5 g, 70%).

Analytical Data:

$[\alpha]^{24}_D$=+271° (c=0.18, CHCl$_3$); $^1$H NMR (400 MHz, CDCl$_3$) δ 7.33 (s, 2H), 7.26 (s, 2H), 7.14 (t, 2H, J=1.97 Hz), 5.51 (d, 2H, J=10.1 Hz), 4.76 (d, 2H, J=10.1 Hz), 4.62 (dd, 2H, J=11.0, 3.69 Hz), 4.32-4.23 (m, 4H), 3.94-3.90 (m, 8H), 3.81-3.64 (m, 4H), 3.16 (ddd, 2H, J=16.3, 11.0, 2.36 Hz), 2.43 (p, 2H, J=5.85 Hz), 1.23-0.92 (m, 4H), 0.02 (s, 18H); $^{13}$C NMR (100 MHz, CDCl$_3$) δ 167.1, 162.7, 151.9, 148.0, 138.4, 133.6, 120.2, 118.8, 111.9, 107.4, 78.6, 67.5, 65.6, 56.7, 56.3, 30.8, 29.0, 18.4, −1.25; IR (ATR, CHCl$_3$) 2958, 1690, 1646, 1605, 1517, 1456, 1428, 1360, 1327, 1207, 1136, 1096, 1060, 1022, 938, 913 cm$^{-1}$; MS (ES$^+$) m/z (relative intensity) 1144 ([M+28]$^+$·, 100), 1117 ([M+H]$^+$·, 48), 1041 (40), 578 (8); HRMS [M+H]$^+$· theoretical $C_{43}H_{54}N_4O_{16}Si_2S_2F_6$ m/z 1117.2491. found (ES$^+$) m/z 1117.2465.

(g) 1,1'-[[(Pentane-1,5-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (8b)

Preparation from 7b according to the above method gave the bis-enol triflate as a pale yellow foam (6.14 g, 82%).

Analytical Data:

(ES+) m/z (relative intensity) 1146 ([M+H]$^+$·, 85).

Example 1

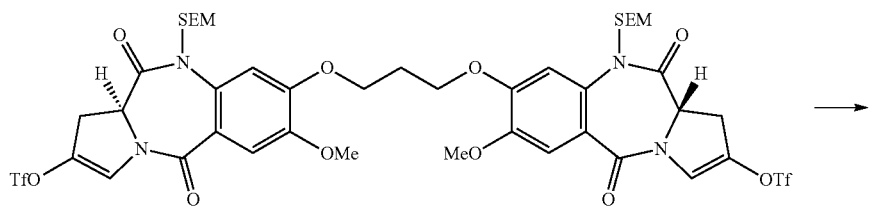

8a

-continued

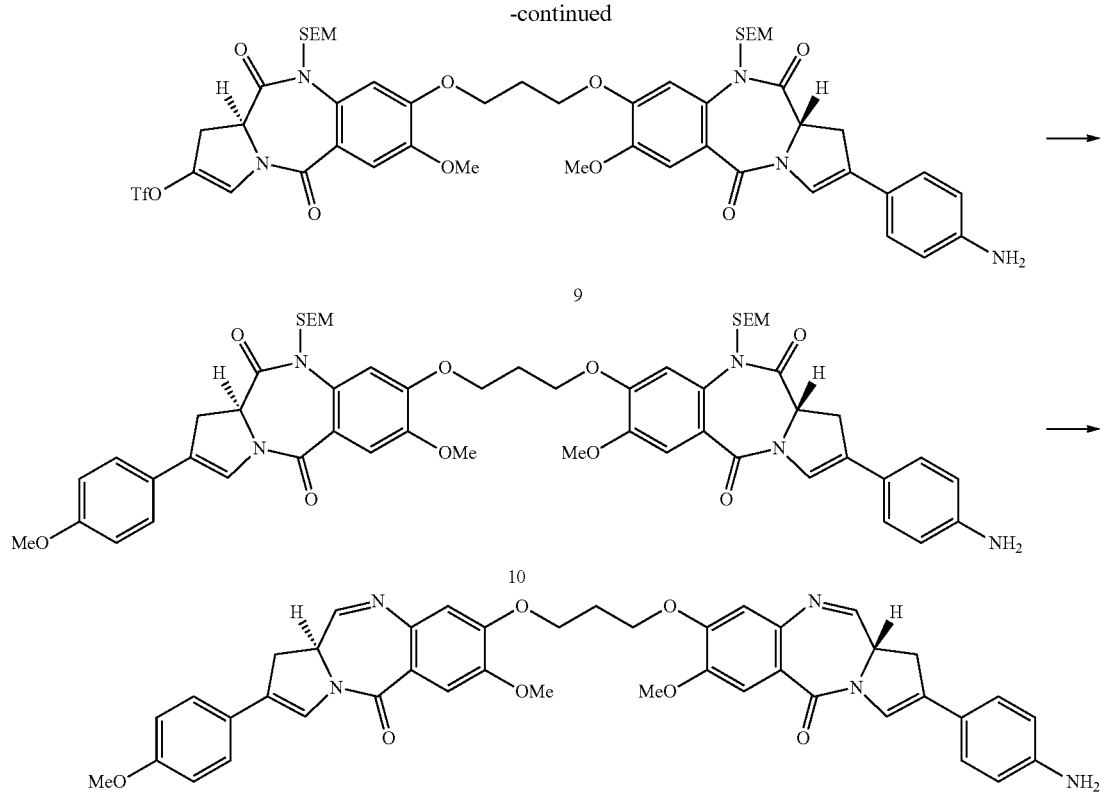

(a) (S)-2-(4-aminophenyl)-7-methoxy-8-(3-((S)-7-methoxy-2-(trifluoromethylsulfonyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)propoxy)-10-((2-(trimethylsilyl)ethoxy)methyl)-1H-pyrrolo[2,1-c][1,4]benzodiazepine-5,11(10H,11aH)-dione (9)

Solid Pd(PPh$_3$)$_4$ (20.18 mg, 17.46 mmol) was added to a stirred solution of the triflate 8a (975 mg, 0.87 mmol), 4-(4,4,5,5-tetramethyl-1,3,2-dioxaboralane-2-yl)aniline (172 mg, 0.79 mmol) and Na$_2$CO$_3$ (138 mg, 3.98 mol) in toluene (13 mL) EtOH (6.5 mL) and H$_2$O (6.5 mL). The dark solution was allowed to stir under a nitrogen atmosphere for 24 hours, after which time analysis by TLC (EtOAc) and LC/MS revealed the formation of the desired mono-coupled product and as well as the presence of unreacted starting material. The solvent was removed by rotary evaporation under reduced pressure and the resulting residue partitioned between H$_2$O (100 mL) and EtOAc (100 mL), after eventual separation of the layers the aqueous phase was extracted again with EtOAc (2×25 mL). The combined organic layers were washed with H$_2$O (50 mL), brine (60 mL), dried (MgSO$_4$), filtered and evaporated in vacuo to provide the crude Suzuki product. The crude Suzuki product was subjected to flash chromatography (40% EtOAc/60% Hexane→70% EtOAc, 30% Hexane). Removal of the excess eluent by rotary evaporation under reduced pressure afforded the desired product 9 (399 mg) in 43% yield.

$^1$H-NMR: (CDCl$_3$, 400 MHz) δ 7.40 (s, 1H), 7.33 (s, 1H), 7.27 (bs, 3H), 7.24 (d, 2H, J=8.5 Hz), 7.15 (t, 1H, J=2.0 Hz), 6.66 (d, 2H, J=8.5 Hz), 5.52 (d, 2H, J=10.0 Hz), 4.77 (d, 1H, J=10.0 Hz), 4.76 (d, 1H, J=10.0 Hz), 4.62 (dd, 1H, J=3.7, 11.0 Hz), 4.58 (dd, 1H, J=3.4, 10.6 Hz), 4.29 (t, 4H, J=5.6 Hz), 4.00-3.85 (m, 8H), 3.80-3.60 (m, 4H), 3.16 (ddd, 1H, J=2.4, 11.0, 16.3 Hz), 3.11 (ddd, 1H, J=2.2, 10.5, 16.1 Hz), 2.43 (p, 2H, J=5.9 Hz), 1.1-0.9 (m, 4H), 0.2 (s, 18H). $^{13}$C-NMR: (CDCl$_3$, 100 MHz) δ 169.8, 168.3, 164.0, 162.7, 153.3, 152.6, 149.28, 149.0, 147.6, 139.6, 134.8, 134.5, 127.9 (methine), 127.5, 125.1, 123.21, 121.5, 120.5 (methine), 120.1 (methine), 116.4 (methine), 113.2 (methine), 108.7 (methine), 79.8 (methylene), 79.6 (methylene), 68.7 (methylene), 68.5 (methylene), 67.0 (methylene), 66.8 (methylene), 58.8 (methine), 58.0 (methine), 57.6 (methoxy), 32.8 (methylene), 32.0 (methylene), 30.3 (methylene), 19.7 (methylene), 0.25 (methyl).

(b) (S)-2-(4-aminophenyl)-7-methoxy-8-(3-((S)-7-methoxy-2-(4-methoxyphenyl)-5,11-dioxo-10-((2-(trimethylsilyl)ethoxy)methyl)-5,10,11,11a-tetrahydro-1H-pyrrolo[2,1-c][1,4]benzodiazepin-8-yloxy) propoxy)-10-((2-(trimethylsilyl)ethoxy)methyl)-1H-pyrrolo[2,1-c][1,4]benzodiazepine-5,11(10H,11aH)-dione (10)

Solid Pd(PPh$_3$)$_4$ (10 mg, 8.69 μmol) was added to a stirred solution of the mono-triflate 9 (230 mg, 0.22 mmol) in toluene (3 mL), EtOH (10 mL), with 4-methoxyphenyl boronic acid (43 mg, 0.28 mmol), Na$_2$CO$_3$ (37 mg, 0.35 mmol), in H$_2$O (1.5 mL) at room temperature. The reaction mixture was allowed to stir under a nitrogen atmosphere for 20 h, at which point the reaction was deemed complete as judged by LC/MS and TLC (EtOAc). The solvent was removed by rotary evaporation under reduced pressure in vacuo and the resulting residue partitioned between EtOAc (75 mL) and H$_2$O (75 mL). The aqueous phase was extracted with EtOAc (3×30 mL) and the combined organic layers washed with H$_2$O (30 mL), brine (40 mL), dried (MgSO$_4$), filtered and evaporated to provide the crude product. The crude product was purified by flash chromatography (60% Hexane: 40% EtOAc→80% EtOAc: 20% Hexane) to provide the pure dimer as an orange foam. Removal of the excess eluent under reduced pressure afforded the desired product 10 (434 mg) in 74% yield.

$^1$H-NMR: (CDCl$_3$, 400 MHz) δ 7.38 (s, 2H), 7.34 (d, 2H, J=8.8 Hz), 7.30 (bs, 1H), 7.26-7.24 (m, 3H), 7.22 (d, 2H, J=8.5 Hz), 6.86 (d, 2H, J=8.8 Hz), 6.63 (d, 2H, J=8.5 Hz), 5.50 (d, 2H, J=10.0 Hz), 4.75 (d, 1H, J=10.0 Hz), 4.74 (d, 1H, J=10.0 Hz), 4.56 (td, 2H, J=3.3, 10.1 Hz), 4.27 (t, 2H, J=5.7 Hz), 4.00-3.85 (m, 8H), 3.80 (s, 3H), 3.77-3.60 (m, 4H), 3.20-3.00 (m, 2H), 2.42 (p, 2H, J=5.7 Hz), 0.96 (t, 4H, J=8.3 Hz), 0.00 (s, 18H).

$^{13}$C-NMR: (CDCl$_3$, 100 MHz) δ 169.8, 169.7, 162.9, 162.7, 160.6, 152.7, 152.6, 149.0, 147.5, 134.8, 127.8 (methine), 127.4, 126.8, 125.1, 123.1, 123.0, 121.5 (methine), 120.4 (methine), 116.4 (methine), 115.5 (methine), 113.1 (methine), 108.6 (methine), 79.6 (methylene), 68.5 (methylene), 66.9 (methylene), 58.8 (methine), 57.6 (methoxy), 56.7 (methoxy), 32.8 (methylene), 30.3 (methylene), 19.7 (methylene), 0.0 (methyl).

(c) (S)-2-(4-aminophenyl)-7-methoxy-8-(3-((S)-7-methoxy-2-(4-methoxyphenyl)-5-oxo-5,11a-dihydro-1H-pyrrolo[2,1-c][1,4]benzodiazepine-8-yloxy)propoxy)-1H-pyrrolo[2,1-c][1,4]benzodiazepine-5 (11aH)-one (11)

Fresh LiBH$_4$ (183 mg, 8.42 mmol) was added to a stirred solution of the SEM-dilactam 10 (428 mg, 0.42 mmol) in THF (5 mL) and EtOH (5 mL) at room temperature. After 10 minutes, delayed vigorous effervescence was observed requiring the reaction vessel to be placed in an ice bath. After removal of the ice bath the mixture was allowed to stir at room temperature for 1 hour. LC/MS analysis at this point revealed total consumption of starting material with very little mono-reduced product. The reaction mixture was poured onto ice (100 mL) and allowed to warm to room temperature with stirring. The aqueous mixture was extracted with DCM (3×30 mL) and the combined organic layers washed with H$_2$O (20 mL), brine (30 mL) and concentrated in vacuo. The resulting residue was treated with DCM (5 mL), EtOH (14 mL), H$_2$O (7 mL) and silica gel (10 g). The viscous mixture was allowed to stir at room temperature for 3 days. The mixture was filtered slowly through a sinter funnel and the silica residue washed with 90% CHCl$_3$: 10% MeOH (~250 mL) until UV activity faded completely from the eluent. The organic phase was washed with H$_2$O (50 mL), brine 60 mL), dried (MgSO$_4$) filtered and evaporated in vacuo to provide the crude material. The crude product was purified by flash chromatography (97% CHCl$_3$: 3% MeOH) to provide the pure C2/C2' aryl PBD dimer 11 (185 mg) 61% yield.

$^1$H-NMR: (CDCl$_3$, 400 MHz) δ 7.88 (d, 1H, J=4.0 Hz), 7.87 (d, 1H, J=4.0 Hz), 7.52 (s, 2H); 7.39 (bs, 1H), 7.37-7.28 (m, 3H), 7.20 (d, 2H, J=8.5 Hz), 6.89 (d, 2H, J=8.8 Hz), 6.87 (s, 1H), 6.86 (s, 1H), 6.67 (d, 2H, J=8.5 Hz), 4.40-4.20 (m, 6H), 3.94 (s, 6H), 3.82 (s, 3H), 3.61-3.50 (m, 2H), 3.40-3.30 (m, 2H), 2.47-2.40 (m, 2H). $^{13}$C-NMR: (CDCl$_3$, 100 MHz) δ 162.5 (imine methine), 161.3, 161.1, 159.3, 156.0, 151.1, 148.1, 146.2, 140.3, 126.2 (methine), 123.2, 122.0, 120.5 (methine), 119.4, 115.2 (methine), 114.3 (methine), 111.9 (methine), 111.2 (methine), 65.5 (methylene), 56.2 (methoxy), 55.4 (methoxy), 53.9 (methine), 35.6 (methylene), 28.9 (methylene).

Example 2

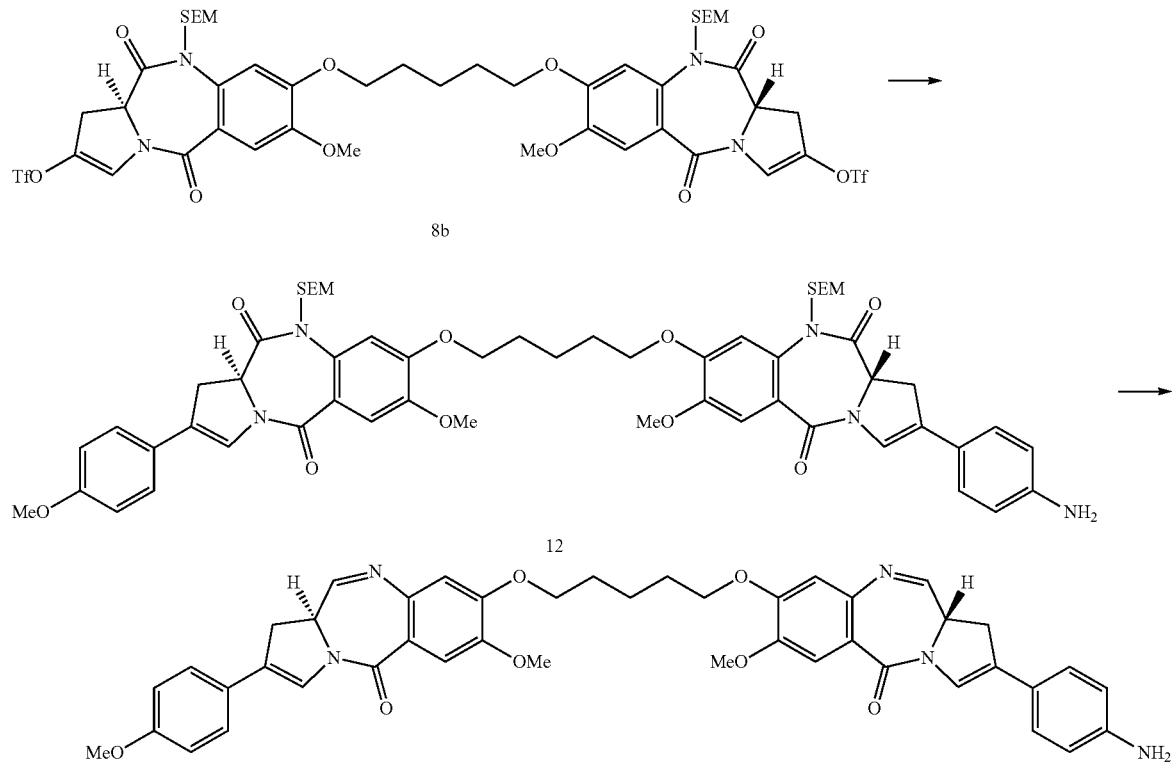

(a) (S)-2-(4-aminophenyl)-7-methoxy-8-(5-((S)-7-methoxy-2-(4-methoxyphenyl)-5,11-dioxo-10-((2-(trimethylsilyl)ethoxy)methyl)-5,10,11,11a-tetrahydro-1H-pyrrolo[2,1-c][1,4]benzodiazepin-8-yloxy) pentyloxy)-10-((2-(trimethylsilyl)ethoxy)methyl)-1H-pyrrolo[2,1-c][1,4]benzodiazepine-5,11(10H,11aH)-dione (12)

Solid Pd(PPh$_3$)$_4$ (32 mg, 27.7 μmol) was added to a stirred solution of the bis-triflate 8b (1.04 g, 0.91 mmol) in toluene (10 mL), EtOH (5 mL), with 4-methoxyphenyl boronic acid (0.202 g, 1.32 mmol), Na$_2$CO$_3$ (0.169 g, 1.6 mmol), in H$_2$O (5 mL) at 30° C. The reaction mixture was allowed to stir under a nitrogen atmosphere for 20 hours. Additional solid 4-(4,4,5,5-tetramethyl-1,3,2-dioxaboralan-2-yl)aniline (0.203 g, 0.93 mmol) and Na$_2$CO$_3$ (0.056 g, 0.53 mmol) were added followed by solid Pd(PPh$_3$)$_4$ (10 mg, 8.6 μmol). The reaction mixture was allowed to stir under a nitrogen atmosphere for a further 20 hours. LC/MS indicated the formation of desired product. EtOAc (100 mL) and H$_2$O (100 mL) were added, the aqueous was separated and extracted with EtOAc (3×30 mL). The combined organic layers were washed with H$_2$O (100 mL), brine (100 mL), dried (MgSO$_4$), filtered and evaporated to provide a dark brown oil. The oil was dissolved in DCM and loaded onto a 10 g SCX-2 cartridge pre-equilibrated with DCM (1 vol). The cartridge was washed with DCM (3 vol), MeOH (3 vol) and the crude product eluted with 2M NH$_3$ in MeOH (2 vol). Flash chromatography (50% n-hexane: 50% EtOAc→20% n-hexane: 80% EtOAc) provided the pure dimer 12 as a yellow foam (0.16 g, 34%).

Analytical Data:
$[\alpha]^{23}_D$=+388° (c=0.22, CHCl$_3$); $^1$H-NMR: (CDCl$_3$, 400 MHz) δ 7.39 (s, 2H), 7.35 (d, 2H, J=12.8 Hz), 7.32 (bs, 1H), 7.26-7.23 (m, 5H), 6.89 (d, 2H, J=8.8 Hz), 6.66 (d, 2H, J=8.5 Hz), 5.55 (d, 2H, J=10.0 Hz), 4.73 (d, 1H, J=10.0 Hz), 4.72 (d, 1H, J=10.0 Hz), 4.62 (td, 2H, J=3.2, 10.4 Hz), 4.15-4.05 (m, 4H), 4.00-3.85 (m, 8H), 3.82 (s, 3H), 3.77-3.63 (m, 4H), 3.20-3.05 (m, 2H), 2.05-1.95 (m, 4H), 1.75-1.67 (m, 2H) 1.01-0.95 (m, 4H), 0.03 (s, 18H); MS (ES$^+$) m/z (relative intensity) 1047 ([M+H]$^+$, 45).

(b) (S)-2-(4-aminophenyl)-7-methoxy-8-(5-((S)-7-methoxy-2-(4-methoxyphenyl)-5-oxo-5,11a-dihydro-1H-pyrrolo[2,1-c][1,4]benzodiazepine-8-yloxy)pentyloxy)-1H-pyrrolo[2,1-c][1,4]benzodiazepine-5 (11aH)-one (13)

Fresh LiBH$_4$ (66 mg, 3.04 mmol) was added to a stirred solution of the SEM-dilactam 12 (428 mg, 0.42 mmol) in THF (3 mL) and EtOH (3 mL) at 0° C. (ice bath). The ice bath was removed and the reaction mixture was allowed to reach room temperature (vigorous effervescence). After 2 hours LC/MS analysis indicated the complete consumption of starting material. The reaction mixture was poured onto ice (50 mL) and allowed to warm to room temperature with stirring. The aqueous mixture was extracted with DCM (3×50 mL) and the combined organic layers washed with H$_2$O (50 mL), brine (50 mL), dried (MgSO$_4$) and concentrated in vacuo. The resulting residue was treated with DCM (2 mL), EtOH (5 mL), H$_2$O (2.5 mL) and silica gel (3.7 g). The viscous mixture was allowed to stir at room temperature for 3 days. The mixture was filtered through a sinter funnel and the silica residue washed with 90% CHCl$_3$: 10% MeOH (~250 mL) until UV activity faded completely from the eluent. The organic phase was dried (MgSO$_4$) filtered and evaporated in vacuo to provide the crude material. The crude product was purified by flash chromatography (99.5% CHCl$_3$: 0.5% MeOH to 97.5% CHCl$_3$: 2.5% MeOH in 0.5% increments)) to provide the pure C2/C2' aryl PBD dimer 13 (59 mg, 52%).

Analytical Data:
$[\alpha]^{28}_D$=+760° (c=0.14, CHCl$_3$); $^1$H NMR (400 MHz, CDCl$_3$) δ 7.89 (d, 1H, J=4.0 Hz), 7.87 (d, 1H, J=4.0 Hz), 7.52 (s, 2H), 7.39 (bs, 1H), 7.37-7.28 (m, 3H), 7.22 (d, 2H, J=8.4 Hz), 6.91 (d, 2H, J=8.8 Hz), 6.815 (s, 1H), 6.81 (s, 1H), 6.68 (d, 2H, J=8.4 Hz), 4.45-4.35 (m, 2H), 4.2-4.0 (m, 4H), 3.94 (s, 6H), 3.85-3.7 (s, 3H), 3.65-3.50 (m, 2H), 3.45-3.3 (m, 2H), 2.05-1.9 (m, 4H), 1.75-1.65 (m, 2H); MS (ES$^+$) (relative intensity) 754.6 ([M+H]$^+$, 100), (ES) (relative intensity) 752.5 ([M−H]$^-$, 100).

Example 3

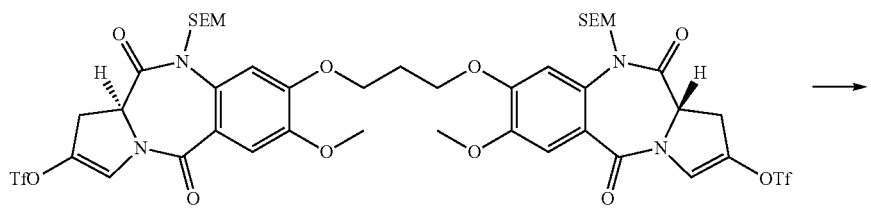

8a

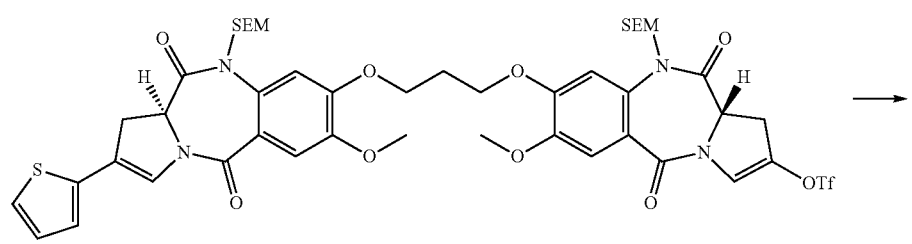

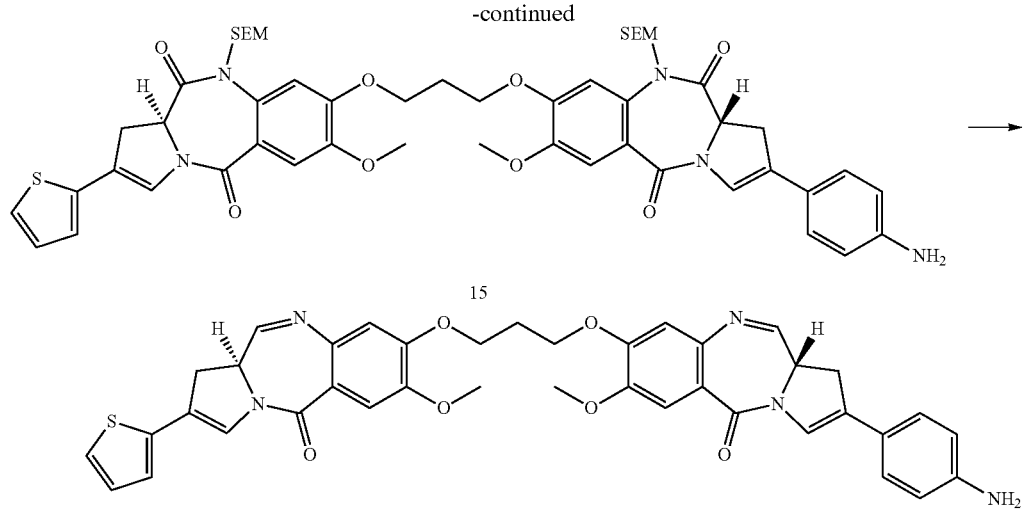

(a) (S)-2-(thien-2-yl)-7-methoxy-8-(3-((S)-7-methoxy-2-(trifluoromethanesulfonyloxy)-5,11-dioxo-10-((2-(trimethylsilyl)ethoxy)methyl)-5,10,11,11a-tetrahydro-1H-pyrrolo[2,1-c][1,4]benzodiazepin-8-yloxy)propyloxy)-10-((2-(trimethylsilyl)ethoxy)methyl)-1H-pyrrolo[2,1-c][1,4]benzodiazepine-5,11(10H,11aH)-dione (14)

Solid Pd(PPh$_3$)$_4$ (41 mg, 0.036 mmol) was added to a stirred solution of the bis-triflate 8a (1 g, 0.9 mmol) in toluene (10 mL), EtOH (5 mL), with thien-2-yl boronic acid (149 mg, 1.16 mmol), Na$_2$CO$_3$ (152 mg, 1.43 mmol), in H$_2$O (5 mL). The reaction mixture was allowed to stir under a nitrogen atmosphere overnight at room temperature. The solvent was removed by evaporation in vacuo and the resulting residue partitioned between H$_2$O (100 mL) and EtOAc (100 mL). The aqueous layer was extracted with EtOAc (2×30 mL) and the combined organic layers washed with H$_2$O (50 mL), brine (50 mL) dried (MgSO$_4$), filtered and evaporated in vacuo to provide the crude product which was purified by flash chromatography (80 hexane: 20 EtOAc→50 hexane: 50 EtOAc) to provide the dimmer 14 (188 mg, 20%) yield Analytical data: LC-MS RT 4.27 mins, 1051 (M+H); $^1$H-NMR (400 MHZ, CDCl$_3$) δ 7.36 (s, 1H), 7.31 (bs, 1H), 7.27 (bs, 1H), 7.26-7.23 (m, 2H), 7.22-7.17 (m, 1H), 7.12 (bs, 1H), 7.02-6.96 (m, 2H), 5.50 (d, J=10.0 Hz, 2H), 7.75 (d, J=10.0 Hz, 2H), 4.65-4.55 (m, 2H), 4.37-4.13 (m, 4H), 4.00-3.85 (m, 8H), 3.8-3.6 (m, 4H), 3.20-3.10 (m, 2H), 2.50-2.35 (m, 2H), 1.0-0.9 (m, 4H), 0 (s, 18H).

(b) (S)-2-(thien-2-yl)-7-methoxy-8-(3-((S)-7-methoxy-2-(trifluoromethanesulfonyloxy)-5,11-dioxo-10-((2-(trimethylsilyl)ethoxy)methyl)-5,10,11,11a-tetrahydro-1H-pyrrolo[2,1-c][1,4]benzodiazepin-8-yloxy)pentyloxy)-10-((2-(trimethylsilyl)ethoxy)methyl)-1H-pyrrolo[2,1-c][1,4]benzodiazepine-5,11(10H,11aH)-dione (15)

Solid Pd(PPh$_3$)$_4$ (7.66 mg, 6.63 μmol) was added to a stirred, cloudy solution of 14 (174 mg, 0.17 mmol), Na$_2$CO$_3$ (28 mg, 0.22 mmol) and 4-(4,4,5,5-tetramethyl-1,3,2-dioxaboralan-2-yl)aniline (47 mg, 0.22 mmol) in toluene (2-5 mL), EtOH (1.25 mL) and H$_2$O (125 mL) at room temperature. The reaction mixture was allowed to stir under a N$_2$ atmosphere for 24 hours at which point the reaction was deemed complete by LC/MS major peak (@ 3.97 min, FW=1016, M+Na) and TLC (EtOAc). The solvent was removed by evaporation in vacuo and the resulting residue partitioned between EtOAc (60 mL) and H$_2$O (30 mL). The layers were separated and the organic phase was washed with H$_2$O (20 mL), brine (30 mL) dried (MgSO$_4$) filtered and evaporated in vacuo to provide the crude product 123 mg, 75% yield.

Analytical data: LC-MS RT 3.98 mins, 100% area, 994 (M+H); $^1$H-NMR (400 MHZ, CDCl$_3$) δ 7.40 (d, J=5.3 Hz, 2H), 7.30 (t, J=1.70 Hz, 1H), 7.29-7.27 (m, 3H), 7.25 (d, J=8.5 Hz, 2H), 7.21 (dd, J=1.4, 4.73 Hz, 1H), 7.03-6.97 (m, 2H), 6.66 (d, J=8.5 Hz, 2H), 5.52 (d, J=10.0 Hz, 2H), 4.78 (d, J=10.0 Hz, 1H), 4.77 (d, J=10.0 Hz, 1H), 4.62 (dd, J=3.4, 10.5 Hz, 1H), 4.59 (dd, J=3.40, 10.6 Hz, 1H), 4.30 (t, J=5.85 Hz, 4H), 3.85-4.03 (m, 8H), 3.84-3.64 (m, 6H), 3.18 (ddd, J=2.2, 10.5, 16.0 Hz, 1H), 3.11 (ddd, J=2.2, 10.5, 16.0 Hz, 1H), 2.44 (p, J=5.85 Hz, 2H), 0.98 (t, J=1.5 Hz, 4H), 0 (s, 18H).

(c) (S)-2-(thien-2-yl)-7-methoxy-8-(3-((S)-7-methoxy-2-(4-aminophenyl)-5-oxo-5,11a-dihydro-1H-pyrrolo[2,1-c][1,4]benzodiazepine-8-yloxy)propyloxy)-1H-pyrrolo[2,1-c][1,4]benzodiazepine-5(11aH)-one (16)

Fresh LiBH$_4$ (47 mg, 2.22 mmol) was added to a stirred solution of the SEM-dilactam 15 (110 mg, 0.11 mmol) in dry THF (3 mL) and EtOH (3 mL) at 0° C. (ice bath). The ice bath was removed and the reaction mixture stirred under a N$_2$ atmosphere for 1 hour. Analysis of the reaction by LC/MS analysis revealed significant formation of the desired product (Pk @2.57 min) (I=69.32), FW=702, M+H) and half-imine. The reaction mixture was allowed to stir for a further 1 hour after which time no further reaction progress was observed by LC/MS. The reaction mixture was poured onto ice, stirred and allowed to warm to room temperature. Following partition between DCM (50 mL) and water (50 mL), the aqueous phase was extracted with DCM (3×20 mL). The combined organic layers were washed with H₂O (50 mL), brine (50 mL) and the solvent removed by evaporation in vacuo under reduced pressure.

The resulting residue was dissolved in DCM (5 mL), EtOH (15 mL) and H₂O (7 mL) then treated with silica gel (5 g). The reaction was allowed to stir at room temperature for 48 h. The silica was removed by filtration through a sinter funnel and the residue rinsed with 90:10 CHCl₃: MeOH (100 mL). H₂O (50 mL) was added to the filtrate and the layers were separated (after shaking). The aqueous layer was extracted with CHCl₃ (2×30 mL) and H₂O (50 mL), brine (50 mL), dried (MgSO₄) filtered and evaporated in vacuo to provide the crude product. Flash chromatography (CHCl₃→98% CHCl₃: 2% MeOH) afforded the product (41 mg, 53%).

Anayltical data: LC-MS RT 2.55 mins, 702 (M+H)

Example 4

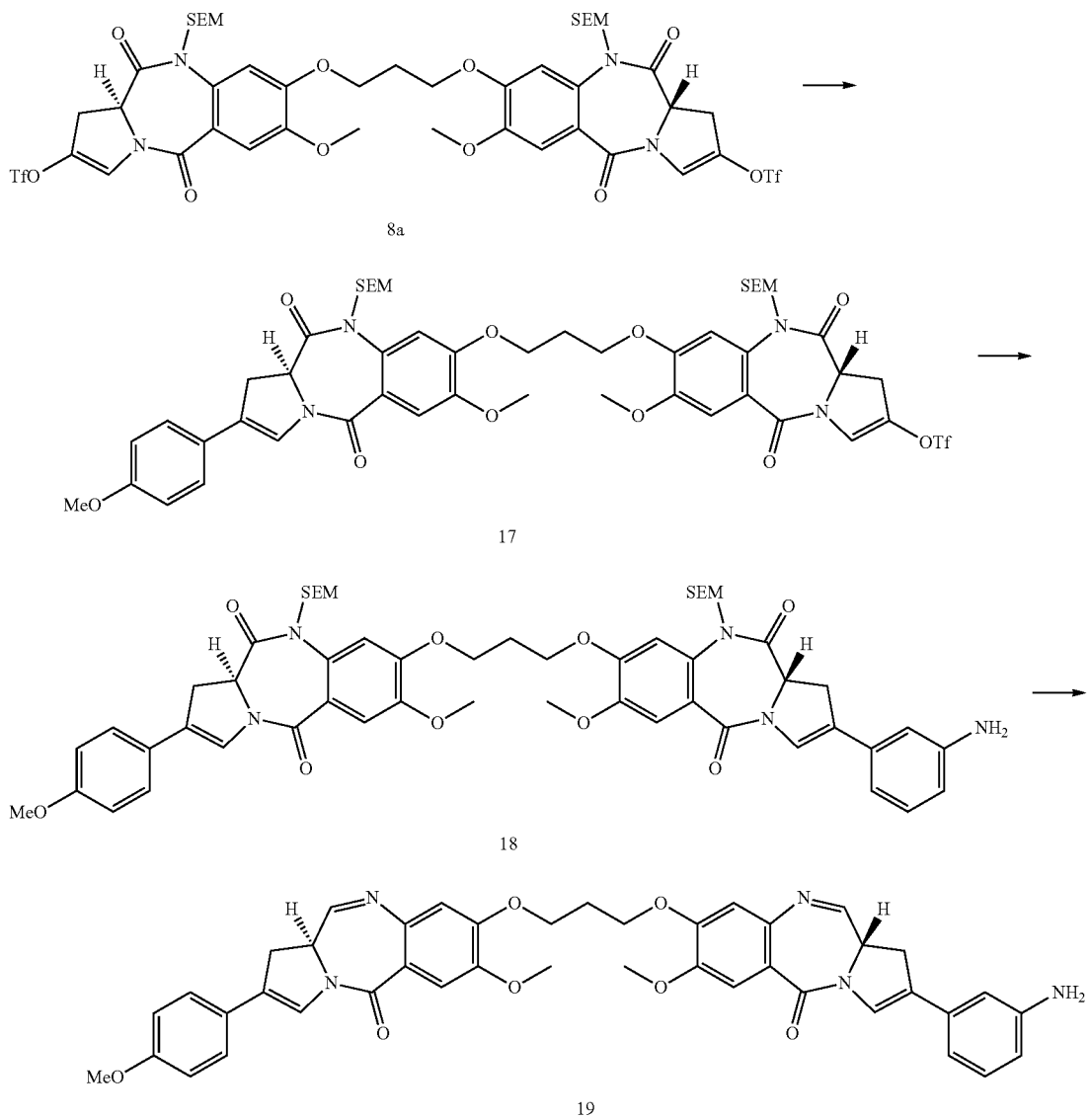

(a) (S)-2-(4-methoxyphenyl)-7-methoxy-8-(3-((S)-7-methoxy-2-(trifluoromethylsulphonyl)-5,11-dioxo-10-((2-(trimethylsilyl)ethoxy)methyl)-5,10,11,11a-tetrahydro-1H-pyrrolo[2,1-c][1,4]benzodiazepin-8-yloxy)propyloxy)-10-((2-(trimethylsilyl)ethoxy)methyl)-1H-pyrrolo[2,1-c][1,4]benzodiazepine-5,11 (10H,11aH)-dione (17)

Solid 4-methoxybenzeneboronic acid (0.388 g, 2.55 mmol) was added to a solution of the SEM protected bis triflate (8a)(3.0 g, 2.69 mmol), sodium carbonate (426 mg, 4.02 mmol) and palladium tetrakis triphenylphosphine (0.08 mmol) in toluene (54.8 mL), ethanol (27 mL) and water (27 mL). The reaction mixture was allowed to stir at room temperature for 3 hours. The reaction mixture was then partitioned between ethyl acetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 30/70→35/65→40/60→45/55) to remove unreacted bis-triflate (0.6 g). Removal of excess eluent from selected fractions afforded the 4-methoxyphenyl coupled product (1.27 g, 1.18 mmol, 41%).

LC-MS RT 4.30 mins, 1076 (M+H); $^1$H-NMR (400 MHZ, CDCl$_3$) δ 7.41 (s, 1H), 7.39 (d, J=8.8 Hz, 2H), 7.35 (s, 1H), 7.34 (bs, 1H), 7.29 (s, 1H), 7.16 (t, J=1.9 Hz, 1H), 6.90 (d, J=8.8 Hz, 2H), 5.53 (d, J=10.0 Hz, 2H), 4.79 (d, J=10.0 Hz, 1H), 4.78 (d, J=10.0 Hz, 1H), 4.66-4.60 (m, 2H), 4.30 (t, J=5.7 Hz, 4H), 4.0-3.94 (m, 2H), 3.93 (s, 3H), 3.92 (s, 3H), 3.84 (s, 3H), 3.83-3.60 (m, 4H), 3.22-3.10 (m, 2H), 2.45 (t, J=5.9 Hz, 2H), 1.05-0.94 (m, 4H), 0 (s, 18H).

(b) (S)-2-(3-aminophenyl)-7-methoxy-8-(3-((S)-7-methoxy-2-(4-methoxyphenyl)-5,11-dioxo-10-((2-(trimethylsilyl)ethoxy)methyl)-5,10,11,11a-tetrahydro-1H-pyrrolo[2,1-c][1,4]benzodiazepin-8-yloxy) propyloxy)-10-((2-(trimethylsilyl)ethoxy)methyl)-1H-pyrrolo[2,1-c][1,4]benzodiazepine-5,11(10H,11 aH)-dione (18)

Solid 3-aminobenzeneboronic acid (0.143 g, 0.92 mmol) was added to a solution of the mono triflate (17)(0.619 g, 0.58 mmol), sodium carbonate (195 mg, 1.84 mmol) and palladium tetrakis triphenylphosphine (26.6 mg, 0.023 mmol) in toluene (10 mL), ethanol (5 mL) and water (5 mL). The reaction mixture was allowed to stir at room temperature for overnight at 30° C. The reaction mixture was then partitioned between ethyl acetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 70/3085/15). Removal of excess eluent from selected fractions afforded the desired product (0.502 g, 0.49 mmol, 85%).

LC-MS RT 4.02 mins, 1019 (M+H); $^1$H-NMR (400 MHZ, CDCl$_3$) δ 7.38-7.35 (m, 4H), 7.33 (bs, 1H), 7.30 (bs, 1H), 7.25 (s, 2H), 7.10 (t, J=7.8 Hz, 1H), 6.88-6.80 (m, 3H), 6.72 (bs, 1H), 6.57 (dd, J=7.9, 1.8 Hz, 1H), 5.50 (d, J=10.0 Hz, 2H), 4.75 (d, 10.0 Hz, 2H), 4.58 (dd, J=10.6, 3.3 Hz, 2H), 4.27 (t, J=5.8 Hz, 4H), 3.95-3.91 (m, 2H), 3.90 (s, 6H), 3.80 (s, 3H), 3.77-3.60 (m, 6H), 3.15-3.05 (m, 2H), 2.41 (p, J=5.8 Hz, 2H), 0.95 (t, =8.25 Hz, 4H), 0 (s, 18H).

(c) (S)-2-(3-aminophenyl)-7-methoxy-8-(3-((S)-7-methoxy-2-(4-methoxyphenyl)-5-oxo-5,11a-dihydro-1H-pyrrolo[2,1-c][1,4]benzodiazepine-8-yloxy)propyloxy)-1H-pyrrolo[2,1-c][1,4]benzodiazepine-5 (11aH)-one (19)

A solution of superhydride (0.56 mL, 0.56 mmol, 1.0 M in THF) was added dropwise to a solution of the SEM dilactam (18)(0.271 g, 0.27 mmol) in dry THF (10 mL) at −78° C. under a nitrogen atmosphere. After 1 hr a further aliquot of superhydride solution (0.13 ml, 0.13 mmol) was added and the reaction mixture was allowed to stir for another 0.5 hr, at which time LC-MS indicated that reduction was complete. The reaction mixture was diluted with water and allowed to warm to room temperature. The reaction mixture was partitioned between chloroform and water, the layers were separated and the aqueous layer extracted with additional chloroform (emulsions). Finally the combined organic phase was washed with brine and dried over magnesium sulphate. The reduced product was dissolved in methanol, chloroform and water and allowed to stir in the presence of silica gel for 72 hours The crude product was subjected to flash column chromatography (methanol/chloroform gradient) to afford the desired imine product (150 mg, 0.21 mmol, 77%) after removal of excess eluent from selected fractions.

LC-MS RT 2.63 mins, 97% area, 726 (M+H); $^1$H-NMR (400 MHZ, CDCl$_3$) δ 7.85 (d, J=3.9 Hz, 1H), 7.84 (d, J=3.9 Hz, 1H), 7.50 (s, 1H), 7.49 (s, 1H), 7.42 (s, 1H), 7.36 (s, 1H), 7.32 (d, J=7.3 Hz, 2H), 7.11 (t, (d, J=7.8 Hz, 1H), 6.90-6.80 (m, 4H), 6.77 (d, J=7.9 Hz, 1H), 4.40-4.20 (m, 6H), 3.92 (s, 6H), 3.80 (s, 3H), 3.60-3.27 (m, 6H), 2.48-2.29 (m, 2H)

Example 5

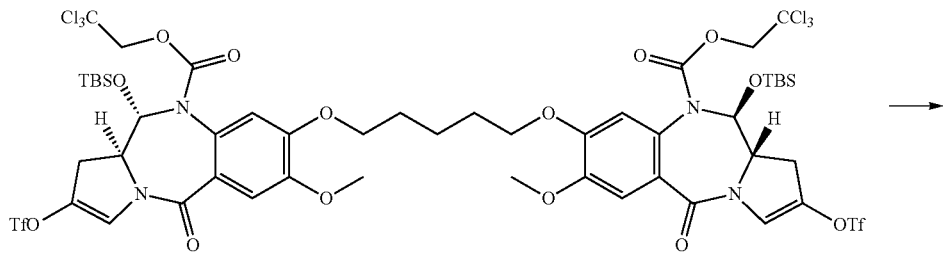

20

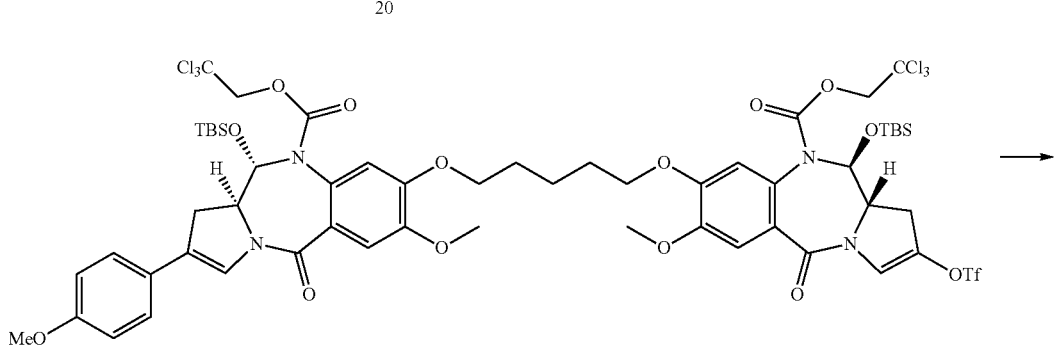

21

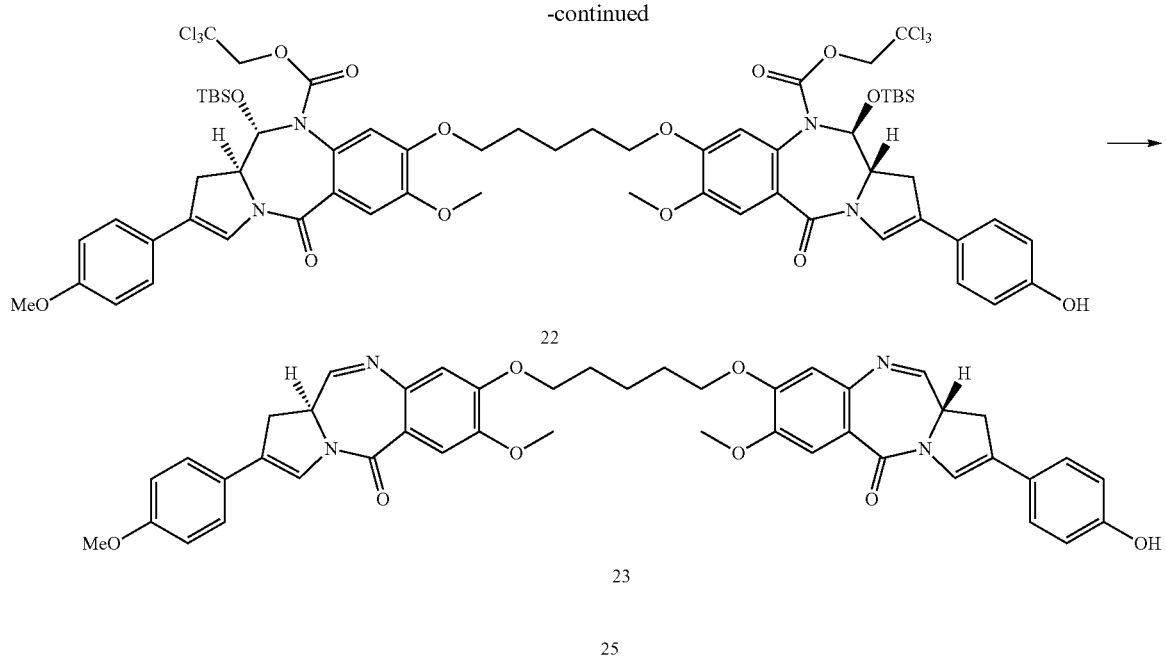

(a) (11S,11aS)-2,2,2-trichloroethyl 11-(tert-bu-tyldimethylsilyloxy)-8-(5-((11 S,11aS)-11-(tert-bu-tyldimethylsilyloxy)-7-methoxy-2-(4-methoxyphenyl)-5-oxo-10-((2,2,2-trichloroethoxy)carbonyl)-5,10,11,11a-tetrahydro-1H-pyrrolo[2,1-c][1,4]benzodiazepin-8-yloxy)pentyloxy)-7-methoxy-5-oxo-2-(trifluoromethylsulfonyloxy)-11,11a-dihydro-pyrrolo[2,1-c][1,4]benzodiazepine-10(5H)-carboxylate 21

Solid 4-methoxybenzeneboronic acid (59 mg, 0.39 mmol) was added to a solution of the Troc protected bis triflate (Compound 44, WO 2006/111759) (600 mg, 0.41 mmol), sodium carbonate (65 mg, 0.61 mmoml) and palladium tetrakis triphenylphosphine (0.012 mmol) in toluene (10.8 mL), ethanol (5.4 mL) and water (5.4 mL). The reaction mixture was allowed to stir at room temperature overnight. The reaction mixture was then partitioned between ethylacetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 20/80→30/70→40/60→60/40) to remove unreacted bis-triflate. Removal of excess eluent from selected fractions afforded the 4-methoxyphenyl coupled product (261 mg, 0.18 mmol, 46%).

LC-MS RT 4.17 mins, 1427 (M+H); $^1$H-NMR (400 MHZ, CDCl$_3$) δ 7.38 (s, 1H), 7.33 (s, 1H), 7.31 (s, 1H), 7.30 (s, 1H), 7.25 (s, 1H), 7.20 (bs, 1H), 6.92 (d, J=8.6 Hz, 2H), 6.77 (d, J=8.7 Hz, 2H), 6.0-5.90 (m, 2H), 5.25 (d, J=12.0 Hz, 1H), 5.24 (d, J=12.0 Hz, 1H), 4.24 (d, J=12.0 Hz, 1H), 4.22 (d, J=12.0 Hz, 1H), 4.18-4.08 (m, 2H), 4.07-3.89 (m, 10H), 3.81 (s, 3H), 3.44-3.25 (m, 2H), 2.85 (d, J=16.6 Hz, 2H), 2.05-1.90 (m, 4H), 1.76-1.64 (m, 2H), 0.93 (s, 9H), 0.90 (s, 9H), 0.30 (s, 6H), 0.26 (s, 6H).

(b) (11S,11aS)-2,2,2-trichloroethyl 11-(tert-bu-tyldimethylsilyloxy)-8-(5-((11S,11aS)-11-(tert-bu-tyldimethylsilyloxy)-2-(4-hydroxyphenyl)-7-methoxy-5-oxo-10-((2,2,2-trichloroethoxy)carbonyl)-5,10,11,11a-tetrahydro-1H-pyrrolo[2,1-c][1,4]benzodiazepin-8-yloxy)pentyloxy)-7-methoxy-2-(4-methoxyphenyl)-5-oxo-11,11a-dihydro-1H-pyrrolo[2,1-c][1,4]benzodiazepine-10(5H)-carboxylate 22

The Suzuki coupling procedure described in step (a) was applied to the synthesis of Compound 21. Compound 20 (62.5 mg 0.044 mmol) was treated with 1 equivalent of 4-hydroxybenzeneboronic acid (10 mg) at 30° C. overnight to afford the desired compound after filtration through a pad of silica gel. (40 mg, 0.029 mmol, 66% yield). The compound was used directly in the subsequent step LC-MS RT 4.27 mins, 1371 (M+H)

(c) (S)-2-(4-hydroxyphenyl)-7-methoxy-8-(5-((S)-7-methoxy-2-(4-methoxyphenyl)-5-oxo-5,11a-dihydro-1H-pyrrolo[2,1-c][1,4]benzodiazepindiazepine-8-yloxy)pentyloxy)-1H-pyrrolo[2,1-c][1,4]benzodiazepine-5(11 aH)-one 23

Cadmium/lead couple (100 mg, Q Dong et al. Tetrahedron Letters vol 36, issue 32, 5681-5682, 1995) was added to a solution of 21 (40 mg, 0.029 mmol) in THF (1 mL) and ammonium acetate (1N, 1 mL) and the reaction mixture was allowed to stir for 1 hour. The reaction mixture was partitioned between chloroform and water, the phases separated and the aqueous phase extracted with chloroform. The combined organic layers were washed with brine and dried over magnesium sulphate. Rotary evaporation under reduced pressure yielded the crude product which was subjected to column chromatography (silica gel, 0→4% MeOH/CHCl$_3$). Removal of excess eluent by rotary evaporation under reduced pressure afforded the desired imine product (17 mg 0.023 mmol 79%).

LC-MS RT 2.20 mins, 755 (M+H); $^1$H-NMR (400 MHZ, CDCl$_3$) δ 7.89 (d, J=3.94 Hz, 1H), 7.89 (d, J=4.00 Hz, 1H), 7.53 (s, 1H), 7.52 (s, 1H), 7.38 (d, J=8.7 Hz, 2H), 7.33 (d, J=8.6 Hz, 2H), 7.28 (s, 1H), 6.90 (d, J=8.7 Hz, 2H), 6.84 (d, J=8.6 Hz, 2H), 6.82 (s, 1H), 6.81 (s, 1H), 5.68 (bs, 1H), 4.50-4.30 (m, 2H), 4.22-4.00 (m, 4H), 3.93 (s, 6H), 3.82 (s, 3H), 3.69-3.45 (m, 2H), 3.44-3.28 (m, 2H), 2.64-1.88 (m, 4H), 1.77-1.62 (m, 2H).

Example 6

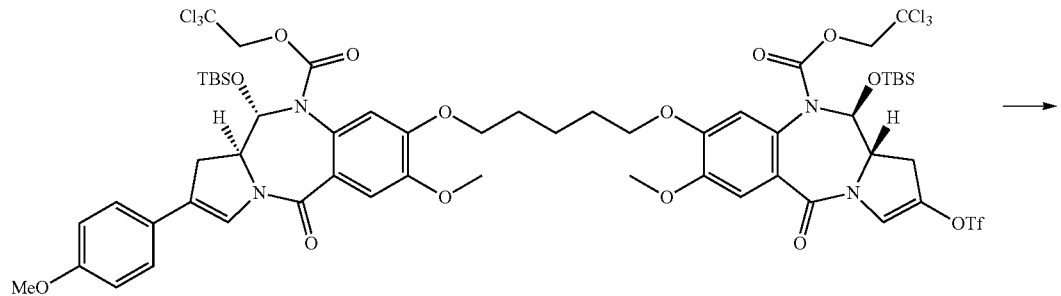

21

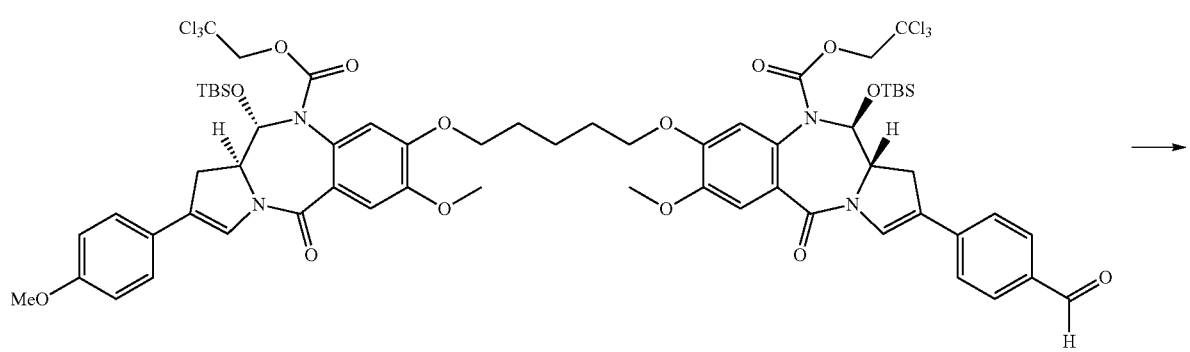

24

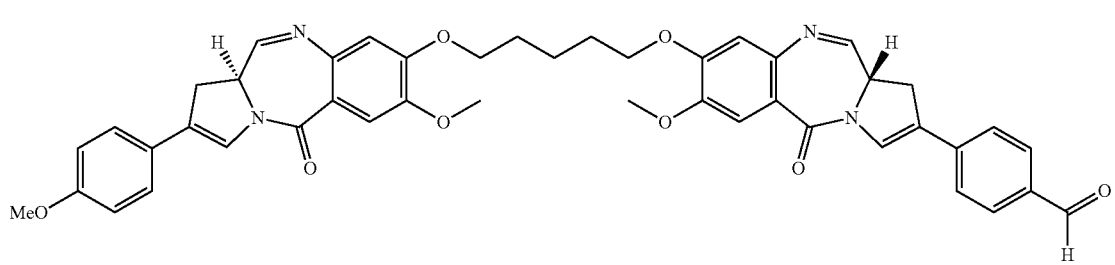

25

(a) (11S,11aS)-2,2,2-trichloroethyl 11-(tert-butyldimethylsilyloxy)-8-(5-((11 S,11a S)-11-(tert-butyldimethylsilyloxy)-2-(4-formylphenyl)-7-methoxy-5-oxo-10-((2,2,2-trichloroethoxy)carbonyl)-5,10,11,11a-tetrahydro-1H-pyrrolo[2,1-c][1,4]benzodiazepin diazepin-8-yloxy)pentyloxy)-7-methoxy-2-(4-methoxyphenyl)-5-oxo-11,11a-dihydro-1H-pyrrolo[2,1-c][1,4]benzodiazepine-10(5H)-carboxylate 24

The Suzuki coupling procedure described in Example 5, step (a), was applied to the synthesis of Compound 24. Compound 21 (62.5 mg, 0.044 mmol) was treated with 1 equivalent of 4-formylbenzeneboronic acid (10.5 mg) at room temperature overnight to afford the desired compound after filtration through a pad of silica gel (45 mg, 0.033 mmol, 75% yield). The compound was used directly in the subsequent step.

LC-MS RT 4.42 mins, 1383 (M+H)

(b) 4-((S)-7-methoxy-8-(5-((S)-7-methoxy-2-(4-methoxyphenyl)-5-oxo-5,11a-dihydro-1H-pyrrolo[2,1-c][1,4]benzodiazepine-8-yloxy)pentyloxy)-5-oxo-5,11a-dihydro-1H-pyrrolo[2,1-c][1,4]benzodiazepine-2-yl)benzaldehyde 25

Compound 24 was deprotected by the method described in Example 5, step (c), to yield the desired compound (18 mg, 0.023 mmol, 79%).

LC-MS RT 3.18 mins, 768 (M+H); $^1$H-NMR (400 MHZ, CDCl$_3$) δ 9.98 (s, 1H), 7.91 (d, J=3.90 Hz, 1H), 7.90-7.80 (m, 3H), 7.68 (s, 1H), 7.60-7.45 (m, 4H), 7.39 (s, 1H), 7.33 (d, J=8.7 Hz, 1H), 6.90 (d, J=8.7 Hz, 2H), 6.83 (s, 1H), 6.82 (s, 1H), 4.55-4.44 (m, 1H), 4.43-4.36 (m, 1H), 4.23-4.00 (m, 4H), 3.95 (s, 3H), 3.94 (s, 3H), 3.82 (s, 3H), 3.66-3.51 (m, 2H), 3.50-3.34 (m, 2H), 2.05-1.87 (m, 4H), 1.76-164 (m, 2H).

Example 7

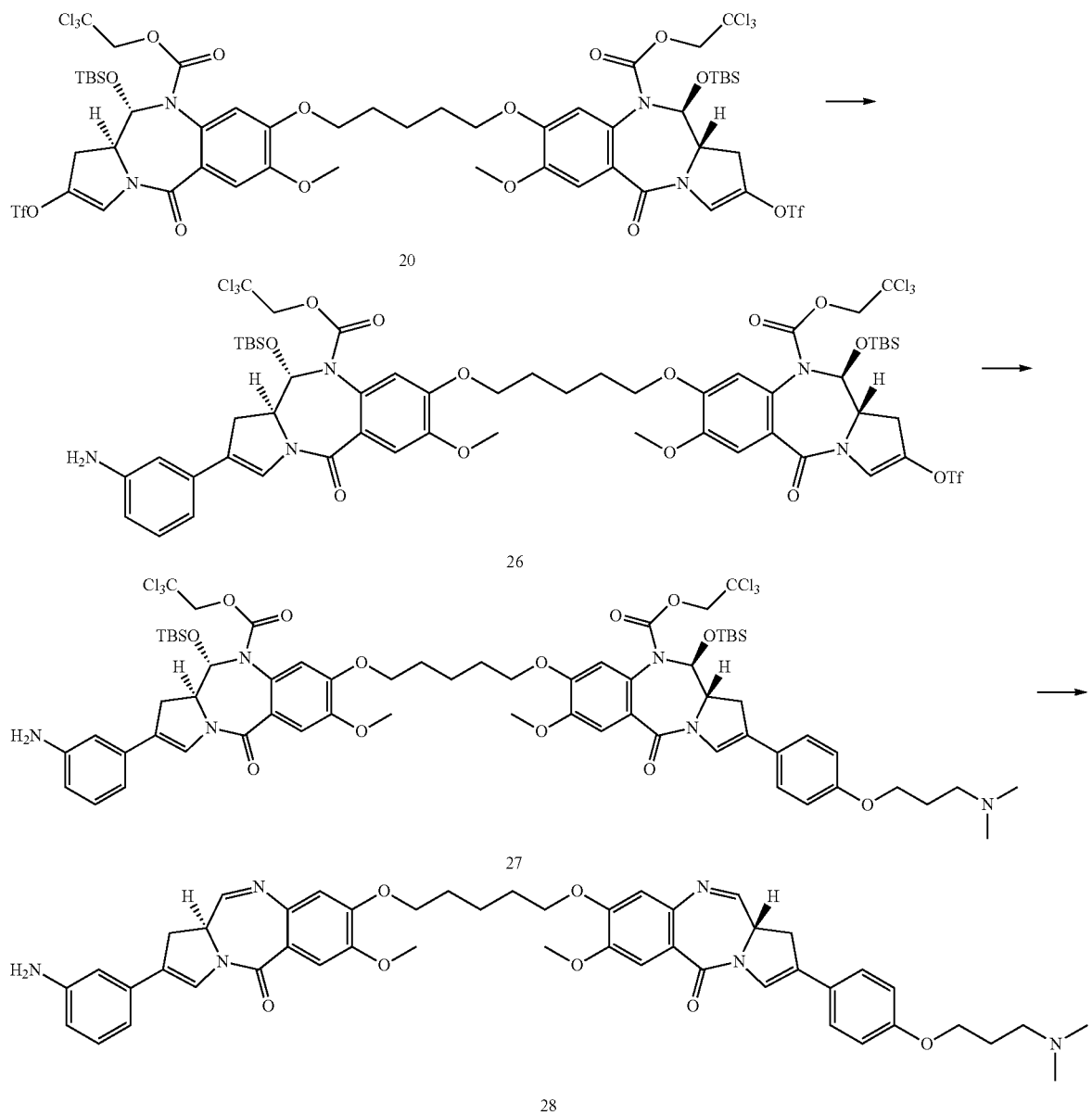

(a) (11S,11a S)-2,2,2-trichloroethyl 2-(3-aminophenyl)-11-(tert-butyldimethylsilyloxy)-8-(5-((11S, 11aS)-11-(tert-butyldimethylsilyloxy)-7-methoxy-5-oxo-10-((2,2,2-trichloroethoxy)carbonyl)-2-(trifluoromethylsulphonyloxy)-5,10,11,11a-tetrahydro-1H-pyrrolo[2,1-c][1,4]benzodiazepindiazepin-8-yloxy)pentyloxy)-7-methoxy-5-oxo-11,11a-dihydro-1H-pyrrolo[2,1-c][1,4]benzodiazepine-10(5H)-carboxylate 26

The Suzuki coupling procedure described in Example 5, step (a), was applied to the synthesis of Compound 26, using 3-aminobenzeneboronic acid to afford the desired compound in 41% yield (230 mg, 0.163 mmol)

LC-MS RT 4.28 mins, 1411 (M+H); $^1$H-NMR (400 MHZ, CDCl$_3$) δ 7.44 (bs, 1H), 7.29 (s, 1H), 7.25 (s, 1H), 7.20 (s, 1H), 7.16 (t, J=7.9 Hz, 1H), 6.84-6.73 (m, 3H), 6.70 (bs, 1H), 6.62 (dd, J=7.9, 1.7 Hz, 1H), 6.66-6.58 (m, 2H), 5.25 (d, J=12.0 Hz, 1H), 5.24 (d, J=12.0 Hz, 1H), 4.24 (d, J=12.0 Hz, 1H), 4.22 (d, J=12.0 Hz, 1H), 4.17-4.07 (m, 2H), 4.08-3.89 (m, 10H), 3.43-3.28 (m, 2H), 2.85 (d, J=1.65 Hz, 2H), 2.07-1.90 (m, 4H), 1.78-1.63 (m, 2H), 0.94 (s, 9H), 0.90 (s, 9H), 0.30 (s, 6H), 0.27 (s, 6H).

(b) (11S,11aS)-2,2,2-trichloroethyl 2-(3-aminophenyl)-11-(tert-butyldimethylsilyloxy)-8-(5-((11S, 11aS)-11-(tert-butyldimethylsilyloxy)-2-(4-(3-(dimethylamino)propoxy)phenyl)-7-methoxy-5-oxo-10-((2,2,2-trichloroethoxy)carbonyl)-5,10,11,11a-tetrahydro-1H-pyrrolo[2,1-c][1,4]benzodiazepindiazepin-8-yloxy)pentyloxy)-7-methoxy-5-oxo-11,11a-dihydro-1H-pyrrolo[2,1-c][1,4]benzodiazepine-10(5H)-carboxylate 27

Solid 4-[3-(dimethylamino)propoxybenzeneboronic acid pinacol ester (25 mg, 0.082 mmol) was added to a solution of 26 (73 mg, 0.052 mmol mmol), sodium carbonate (18 mg, 0.17 mmol) and palladium tetrakis triphenylphosphine (3 mg) in toluene (1 mL), ethanol (0.5 mL) and water (0.5 mL). The reaction mixture was allowed to stir at room temperature overnight. The reaction mixture was then partitioned between ethyl acetate and water. The organic layer was washed with water and brine and dried over magnesium sulphate. Excess solvent was removed by rotary evaporation under reduced pressure and the resulting residue was eluted through a plug of silica gel with chloroform/methanol. Removal of excess eluent from selected fractions afforded the 4-methoxyphenyl coupled product (50 mg, 0.035 mmol, 67%).

LC-MS RT 4.12 mins, 1440 (M+H)

(c) (S)-2-(3-aminophenyl)-8-(5-((S)-2-(4-(3-(dimethylamino)propoxy)phenyl)-7-methoxy-5-oxo-5,11a-dihydro-1H-pyrrolo[2,1-c][1,4]benzodiazepine-8-yloxy)pentyloxy)-7-methoxy-1H-pyrrolo[2,1-c][1,4]benzodiazepine-5(11aH)-one 28

Compound 27 was deprotected by the method described in Example 5, step (c), to yield the desired compound. The reaction mixture was partitioned between DCM and aqueous sodium hydrogen carbonate (emulsion) and the crude product purified by gradient column chromatography on silica gel (5% methanol chloroform→35% methanol/chloroform) to afford the desired unsymmetrical PBD imine (50 mg, 0.018 mmol, 58%)

LC-MS RT 2.55 mins, 826 (M+H); $^1$H-NMR (400 MHZ, CDCl$_3$) δ 7.92-7.82 (m, 2H), 7.52 (bs, 2H), 7.45 (bs, 1H), 7.39 (bs, 1H), 7.31 (d, J=8.6 Hz, 2H), 7.14 (t, J=7.8 Hz, 1H), 6.89 (d, J=8.6 Hz, 2H), 6.85-6.75 (m, 3H), 6.72 (bs, 1H), 6.60 (d, J=8.0 Hz, 1H), 4.46-4.33 (m, 2H), 4.21-3.98 (m, 6H), 3.94 (s, 6H), 3.63-3.50 (m, 2H), 3.43-3.29 (m, 2H), 2.64-2.48 (m, 2H), 2.34 (s, 6H), 2.10-1.89 (m, 6H), 1.57 (m, 2H).

Example 8

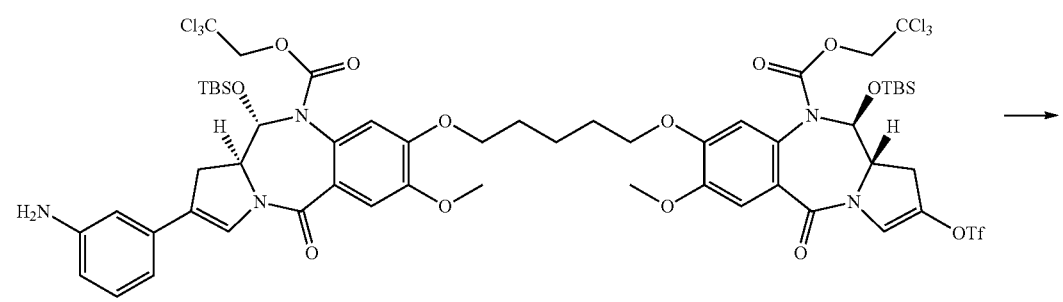

26

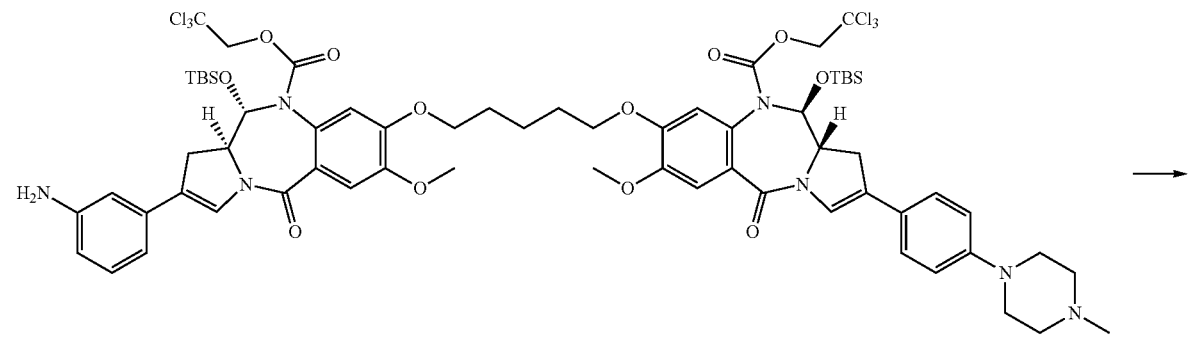

29

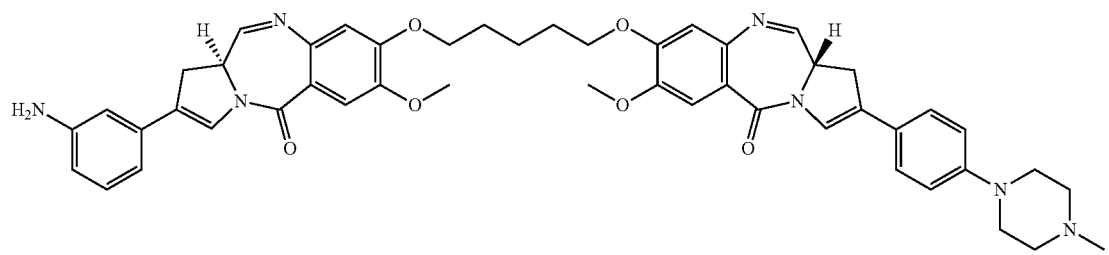

30

(a) (11S,11aS)-2,2,2-trichloroethyl 2-(3-aminophenyl)-11-(tert-butyldimethylsilyloxy)-8-(5-((11S,11aS)-11-(tert-butyldimethylsilyloxy)-7-methoxy-2-(4-(4-methylpiperazin-1-yl)phenyl)-5-oxo-10-((2,2,2-trichloroethoxy)carbonyl)-5,10,11,11a-tetrahydro-1H-pyrrolo[2,1-c][1,4]benzodiazepin diazepin-8-yloxy)pentyloxy)-7-methoxy-5-oxo-11,11a-dihydro-1H-pyrrolo[2,1-c][1,4]benzodiazepine-10(5H)-carboxylate 29

The method of Example 7, step (b), was performed to afford the desired product (58 mg, 0.040 mmol, 78%) after filtration through a plug of silica gel (with 1/3 methanol/chloroform) and removal of excess solvent by rotary evaporation under reduced pressure.

LC-MS RT 4.08 mins, 1439 (M+H)

methanol/chloroform) to afford the desired unsymmetrical PBD imine (18 mg, 0.022 mmol, 59%)

LC-MS RT 2.52 mins, 823 (M+H); $^1$H-NMR (400 MHZ, CDCl$_3$) δ 7.80 (d, J=3.8 Hz, 2H), 7.45 (s, 2H), 7.38 (s, 1H), 7.30 (s, 1H), 7.23 (d, J=8.6 Hz, 2H), 7.07 (t, J=7.8 Hz, 1H), 6.83 (d, J=8.6 Hz, 2H), 6.79-6.89 (m, 3H), 6.65 (s, 1H), 6.54 (d, J=7.9 Hz, 1H), 4.40-4.24 (m, 2H), 4.15-3.93 (m, 4H), 3.87 (s, 6H), 3.56-3.42 (m, 2H), 3.37-3.23 (m, 2H), 3.22-3.08 (m, 4H), 2.61-2.41 (m, 4H), 2.29 (s, 3H), 1.98-1.80 (m, 4H), 1.67-1.54 (m, 2H).

Example 9

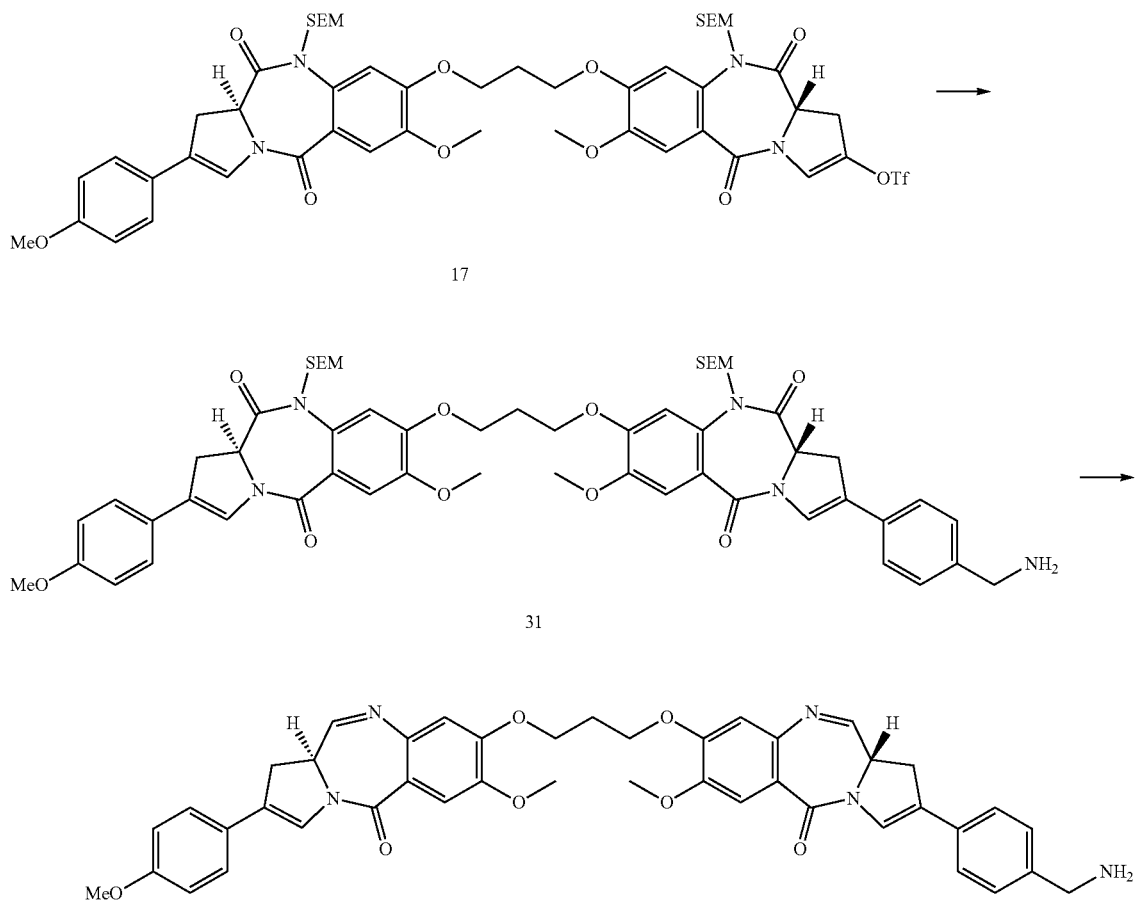

(b) (S)-2-(3-aminophenyl)-7-methoxy-8-(5-((S)-7-methoxy-2-(4-(4-methylpiperazin-1-yl)phenyl)-5-oxo-5,11a-dihydro-1H-pyrrolo[2,1-c][1,4]benzodiazepine-8-yloxy)pentyloxy)-1H-pyrrolo[2,1-c][1,4]benzodiazepine-5(11aH)-one 30

The method of Example 7, step (c) was used to deprotect compound 29. The crude product was purified by silica gel gradient chromatography (2% methanol chloroform-35%

(a) (S)-2-(4-(aminomethyl)phenyl)-7-methoxy-8-(3-((7-methoxy-2-(4-methoxyphenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propyloxy)-10-((2-(trimethylsilyl)ethoxy)methyl)-1H-pyrrolo[2,1-c][1,4]benzodiazepine-5,11(10H, 11aH)-dione 31

Solid 4-aminomethylbenzeneboronic acid hydrochloride (0.111 g, 0.59 mmol) was added to a solution of 17 (0.394 g, 0.37 mmol), sodium carbonate (175 mg, 1.654 mmol) and palladium tetrakis triphenylphosphine (28.0 mg, 0.024 mmol) in toluene (10 mL), ethanol (5 mL) and water (5 mL). The reaction mixture was allowed to stir overnight at 30° C. The following day the reaction mixture was heated for a further 3 hours at 70° C. The reaction mixture was then partitioned between ethyl acetate and water. The organic layer was washed with water and brine and dried over magnesium sulphate. Excess solvent was removed by rotary evaporation under reduced pressure and the resulting residue was subjected to flash column chromatography (silica gel; gradient elution EtOAc/hexane 2/98→05/85). Removal of excess eluent from selected fractions afforded the desired product (0.230 mg, 0.22 mmol, 61%).

LC-MS RT 3.63 mins, 1034 (M+2H); $^1$H-NMR (400 MHz, DMSO d$_6$) δ 11.7 (s, 2H), 7.52 (d, J=8.2 Hz, 2H), 7.48 (d, J=8.7 Hz, 2H), 7.40 (s, 1H), 7.50 (d, J=8.1 Hz, 2H), 7.38-7.19 (m, 5H) 6.93 (d, J=8.7 Hz, 2H), 5.40 (d, J=2.13 Hz, 1H), 5.38 (d, J=2.12 Hz, 1H), 5.32 (d, J=10.6 Hz, 2H), 5.25 (d, J=10.6 Hz, 2H), 4.87-4.72 (m, 2H), 4.35-4.15 (m, 4H), 3.85 (s, 6H), 3.79 (s, 3H), 3.73-3.56 (m, 2H), 3.55-3.39 (m, 4H), 3.22-3.02 (m, 2H), 2.39-2.23 (m, 2H), 0.94-0.67 (m, 4H), −0.06 (s, 18H).

(b) (S)-2-(4-(aminomethyl)phenyl)-7-methoxy-8-(3-((S)-7-methoxy-2-(4-methoxyphenyl)-5-oxo-5,11a-dihydro-1H-pyrrolo[2,1-c][1,4]benzodiazepine-8-yloxy)propyloxy)-1H-pyrrolo[2,1-c][1,4] benzodiazepine-5(11aH)-one 32

Compound 31 was deprotected following the method of Example 1, step (c). The crude product was purified by gradient column chromatography (5/95→30/70 MeOH/CHCl$_3$) to afford the product as a mixture of imine and carbinolamine methyl ethers.

LC-MS RT 2.58 mins, 740 (M+H).

Example 10

(S)-2-(4-aminophenyl)-7-methoxy-11(S)-sulpho-8-(3-((S)-7-methoxy-11(S)-sulpho-2-(4-methoxyphenyl)-5-oxo-5,10,11,11a-tetrahydro-1H-pyrrolo[2,1-c][1,4]benzodiazepine-8-yloxy)propyloxy)-1H-pyrrolo[2,1-c][1,4]benzodiazepine-5(11aH)-one disodium salt 33

Sodium bisulphite (8.5 mg, 3.1 eq) was added to a stirred suspension of bis-imine 11 (20 mg, 0.036 mmol) in isopropanol (4 mL) and water (2 mL). The reaction mixture was allowed to stir vigorously and eventually became clear (c, 1 hour). The reaction mixture was transferred to a funnel and filtered through a cotton wall (and then washed with 2 mL water). The filtrate was flash frozen (liquid and to bath) and lyophilized to afford the desired product 33 in quantitative yield.

LC-MS RT 11.77 mins, 727.2 (M+H) (Mass of parent compound, bisulphite adducts unstable in mass spectrometer); $^1$H-NMR (400 MHz, CDCl$_3$) δ 7.66-7.55 (m, 5H), 7.43 (s, 1H), 7.39 (d, J=8.66 Hz, 2H), 7.06 (m, 2H), 6.93 (d, J=8.84 Hz, 2H), 6.54 (m, 2H), 5.29-5.21 (m, 2H), 4.32-4.28 (m, 2H), 4.14-4.20 (m, 4H), 3.96-3.83 (m, 2H), 3.77 (s, 3H), 3.73 (m, 6H), 3.52-3.43 (m, 2H), 3.30-3.08 (m, 2H), 2.24-2.21 (m, 2H).

Example 11

Determination of In Vitro Cytotoxicity

K562 Assay

K562 human chronic myeloid leukaemia cells were maintained in RPM1 1640 medium supplemented with 10% fetal calf serum and 2 mM glutamine at 37° C. in a humidified atmosphere containing 5% CO$_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates (10$^4$ cells per well, 8 wells per sample). Plates were then kept in the dark at 37° C. in a humidified atmosphere containing 5% CO$_2$. The assay is based on the ability of viable cells to reduce a yellow soluble tetrazolium salt, 3-(4,5-dimethylthiazol-2-yl)-2,5-

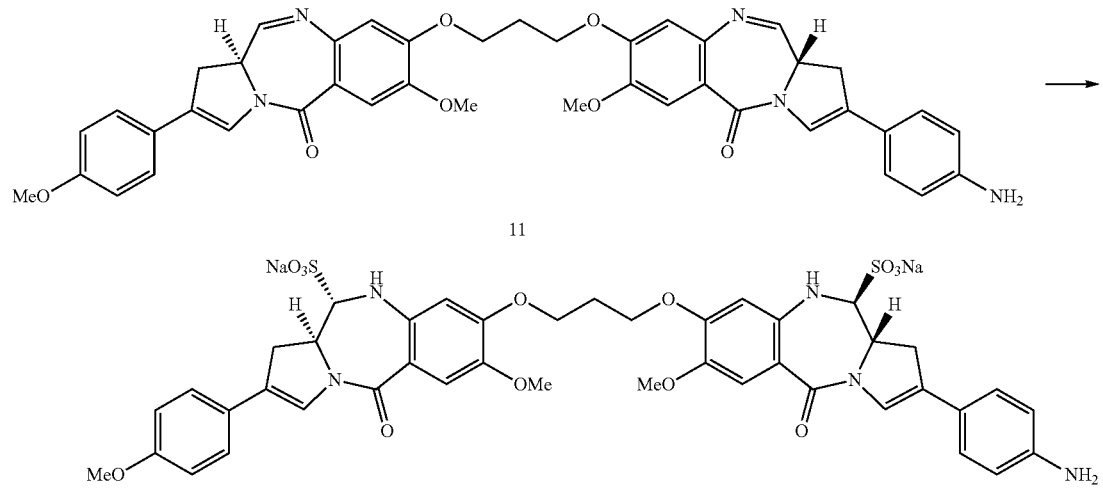

diphenyl-2H-tetrazolium bromide (MTT, Aldrich-Sigma), to an insoluble purple formazan precipitate. Following incubation of the plates for 4 days (to allow control cells to increase in number by approximately 10 fold), 20 μL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

Compound 13 has an $IC_{50}$ of 30 μM in this assay.

A2780 assay

A2780 parental cell line was grown in Dulbecco's Modified Eagles' Media (DMEM) containing ~10% Foetal Calf Serum (FCS) and ~1% 200 mM L-Glutamine solution and grown in Corning Cellbind 75 cm² flasks.

190 μl cell suspension was added (at 1×10⁴) to each well of columns 2 to 11 of a 96 well plate (Nunc 96F flat bottom TC plate). 190 μl of media was added to each well of columns 1 and 12. The media was Dulbecco's Modified Eagles' Media (DMEM) (which included ~10% Foetal Calf Serum (FCS) and ~1% 200 mM L-Glutamine solution).

Plates were incubated overnight at 37° C. before addition of drug if cells were adherent. 200 μM of the test compound solutions (in 100% DMSO) were serially diluted across a 96 well plate. Each resulting point was then further diluted 1/10 into sterile distilled water (SDW).

To the cell negative blanks and compound negative control wells, 10% DMSO was added at 5% v/v. Assay plates were incubated for the following durations at 37° C. in 5% $CO_2$ in a humidified incubator for 72 hours. Following incubation, MTT solution to a final concentration of 1.5 μM was added to each well. Plates were then incubated for a further 4 hours at 37° C. in 5% $CO_2$ in a humidified incubator. The media was then removed, and the dye was solubilised in 200 μl DMSO (99.99%).

Plates were read at 540 nm absorbance using an Envision plate reader. Data was analysed using Microsoft Excel and GraphPad Prism and $IC_{50}$ values obtained.

Compound II has an $IC_{50}$ of 11.7 μM in this assay.

The invention claimed is:

1. A compound with the formula I:

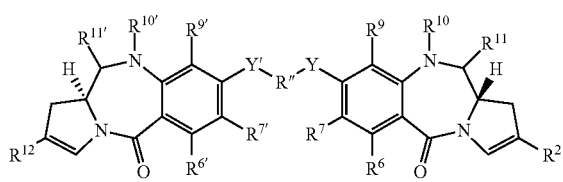

I wherein:
$R^2$ is of formula II:

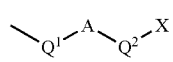

II where A is a $C_{5-7}$ aryl group, X is selected from the group consisting of: OH, SH, $CO_2H$, COH, N=C=O, $NHR^N$, wherein $R^N$ is selected from the group consisting of H and $C_{1-4}$ alkyl, and $(OC_2H_4)_mOCH_3$, where m is 1 to 3, and either:
  (i) $Q^1$ is a single bond, and $Q^2$ is selected from the group consisting of a single bond and —Z—$(CH_2)_n$—, where Z is selected from the group consisting of a single bond, O, S and NH and n is from 1 to 3; or
  (ii) $Q^1$ is —CH=CH—, and $Q^2$ is a single bond;
$R^{12}$ is a $C_{5-10}$ aryl group, optionally substituted by one or more substituents selected from the group consisting of: halo, nitro, cyano, ether, $C_{1-7}$ alkyl, $C_{3-7}$ heterocyclyl and bis-oxy-$C_{1-3}$ alkylene;
$R^6$ and $R^9$ are independently selected from the group consisting of H, R, OH, OR, SH, SR, $NH_2$, NHR, NRR', nitro, $Me_3Sn$ and halo;
where R and R' are independently selected from the group consisting of optionally substituted $C_{1-12}$ alkyl, $C_{3-20}$ heterocyclyl and $C_{5-20}$ aryl groups;
$R^7$ is selected from the group consisting of H, R, OH, OR, SH, SR, $NH_2$, NHR, NHRR', nitro, $Me_3Sn$ and halo;
either:
  (a) $R^{10}$ is H, and $R^{11}$ is OH, or $OR^A$, where $R^A$ is $C_{1-4}$ alkyl;
  (b) $R^{10}$ and $R^{11}$ form a nitrogen-carbon double bond between the nitrogen and carbon atoms to which they are bound; or
  (c) $R^{10}$ is H and $R^{11}$ is $SO_zM$, where z is 2 or 3 and M is a monovalent pharmaceutically acceptable cation;
R" is a $C_{3-12}$ alkylene group, which chain may be interrupted by one or more heteroatoms selected from the group consisting of O, S, and NH, and/or aromatic rings selected from benzene or pyridine;
Y and Y' are independently selected from the group consisting of O, S, or NH;
$R^{6'}, R^{7'}, R^{9'}$ are selected from the same groups as $R^6, R^7$ and $R^9$ respectively and $R^{10'}$ and $R^{11'}$ are the same as $R^{10}$ and $R^{11}$, wherein if $R^{11}$ and $R^{11'}$ are $SO_zM$, M represents a divalent pharmaceutically acceptable cation selected from $Ca^{2+}$ and $Mg^{2+}$.

2. A compound according to claim 1, wherein $R^7$ is selected from H, OH and OR.

3. A compound according to claim 2, wherein $R^7$ is a $C_{1-4}$ alkyloxy group.

4. A compound according to claim 1, wherein Y is O.

5. A compound according to claim 1, wherein R" is $C_{3-7}$ alkylene.

6. A compound according to claim 1, wherein $R^9$ is H.

7. A compound according to claim 1, wherein $R^6$ is selected from H and halo.

8. A compound according to claim 1, wherein A is phenyl.

9. A compound according to claim 1, wherein X is selected from OH, SH, or $NH_2$.

10. A compound according to claim 1, wherein $Q^1$ is a single bond.

11. A compound according to claim 10, wherein $Q^2$ is a single bond.

12. A compound according to claim 10, wherein $Q^2$ is —Z—$(CH_2)_n$—, Z is O or S and n is 1 or 2.

13. A compound according to claim 1, wherein $Q^1$ is —CH=CH—.

14. A compound according to claim 1, wherein $R^{12}$ is a $C_{5-7}$ aryl group.

15. A compound according to claim 14, wherein $R^{12}$ is phenyl.

16. A compound according to claim 1, wherein $R^{12}$ is a $C_{8-10}$ aryl group.

17. A compound according to claim 1, wherein $R^{12}$ bears one to three substituent groups.

18. A compound according to claim 1, wherein $R^{10}$ and $R^{11}$ and form a nitrogen-carbon double bond.

19. A compound according to claim 1, wherein $R^{6'}, R^{7'}, R^{9'}, R^{10'}, R^{11'}$ and Y' are the same as $R^6, R^7, R^9, R^{10}, R^{11}$ and Y respectively.

20. A compound of formula II:

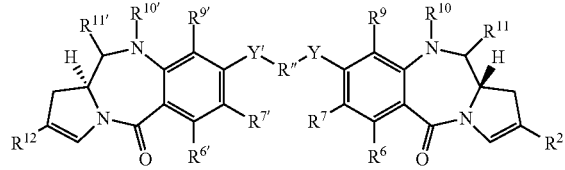

II wherein:
$R^2$ is

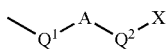

where A is a $C_{5-7}$ aryl group, X is selected from the group consisting of: OH, SH, $CO_2H$, COH, N=C=O, $NHR^N$, wherein $R^N$ is selected from the group consisting of H and $C_{1-4}$ alkyl, and $(OC_2H_4)_mOCH_3$, where m is 1 to 3, and either:
(i) $Q^1$ is a single bond, and $Q^2$ is selected from a single bond or —Z—$(CH_2)_n$—, where Z is selected from a single bond, O, S or NH and is from 1 to 3; or
(ii) $Q^1$ is —CH=CH—, and $Q^2$ is a single bond;
$R^{12}$ is a $C_{5-10}$ aryl group, optionally substituted by one or more substituents selected from the group consisting of: halo, nitro, cyano, ether, $C_{1-7}$ alkyl, $C_{3-7}$ heterocyclyl and bis-oxy-$C_{1-3}$ alkylene;
$R^6$ and $R^9$ are independently selected from the group consisting of H, R, OH, OR, SH, SR, $NH_2$, NHR, NRR', nitro, $Me_3Sn$ and halo;
where R and R' are independently selected from the group consisting of optionally substituted $C_{1-12}$ alkyl, $C_{3-20}$ heterocyclyl and $C_{5-20}$ aryl groups;
$R^7$ is selected from the group consisting of H, R, OH, OR, SH, SR, $NH_2$, NHR, NHRR', nitro, $Me_3Sn$ and halo; either:

(a) $R^{10}$ is carbamate nitrogen protecting group, and $R^{11}$ is O-Prot°, wherein Prot° is an oxygen protecting group;
(b) $R^{10}$ is a hemi-aminal nitrogen protecting group and $R^{11}$ is an oxo group;
R" is a $C_{3-12}$ alkylene group, which chain may be interrupted by one or more heteroatoms, selected from the group consisting of O, S, and $NR^{N2}$ (where $R^{N2}$ is H or $C_{1-4}$ alkyl), and/or aromatic rings, e.g. benzene or pyridine;
Y and Y' are selected from O, S, or NH;
$R^{6'}, R^{7'}, R^{9'}$ are selected from the same groups as $R^6, R^7$ and $R^9$ respectively and $R^{10'}$ and $R^{11'}$ are the same as $R^{10}$ and $R^{11}$.

21. A compound according to claim 20, wherein $R^7$ is selected from H, OH or OR.

22. A compound according to claim 21, wherein $R^7$ is a $C_{1-4}$ alkyloxy group.

23. A compound according to claim 20, wherein Y is O.

24. A compound according to claim 20, wherein R" is $C_{3-7}$ alkylene.

25. A compound according to claim 20, wherein $R^9$ is H.

26. A compound according to claim 20, wherein $R^6$ is selected from H or halo.

27. A compound according to claim 20, wherein A is phenyl.

28. A compound according to claim 20, wherein X is selected from OH, SH, or $NH_2$.

29. A compound according to claim 20, wherein $Q^1$ is a single bond.

30. A compound according to claim 29, wherein $Q^2$ is a single bond.

31. A compound according to claim 29, wherein $Q^2$ is —Z—$(CH_2)_n$—, Z is O or S and n is 1 or 2.

32. A compound according to claim 20, wherein $Q^1$ is —CH=CH—.

33. A compound according to claim 20, wherein $R^{12}$ is a $C_{5-7}$ aryl group.

34. A compound according to claim 33, wherein $R^{12}$ is phenyl.

35. A compound according to claim 20, wherein $R^{12}$ is a $C_{8-10}$ aryl group.

36. A compound according to claim 20, wherein $R^{12}$ bears one to three substituent groups.

37. A compound according to claim 20, wherein $R^{10}$ is Troc.

38. A compound according to claim 20, wherein $R^{11}$ is OTBS.

39. A compound according to claim 20, wherein $R^{11}$ is oxo and $R^{10}$ is SEM.

40. A compound according to claim 20, wherein $R^{6'}, R^{7'}, R^{9'}, R^{10'}, R^{11'}$ and Y' are the same as $R^6, R^7, R^9, R^{10}, R^{11}$ and Y respectively.

41. A compound of the formula:

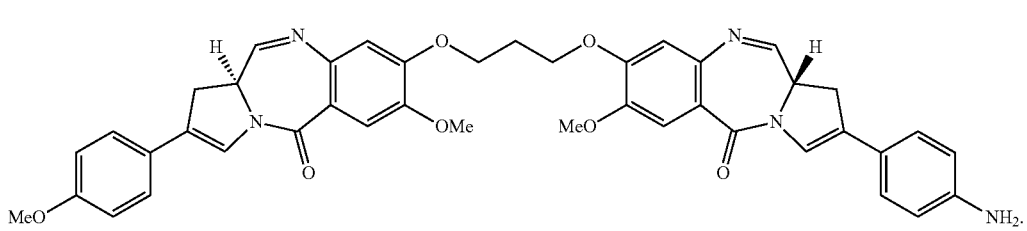

42. A compound of the formula:
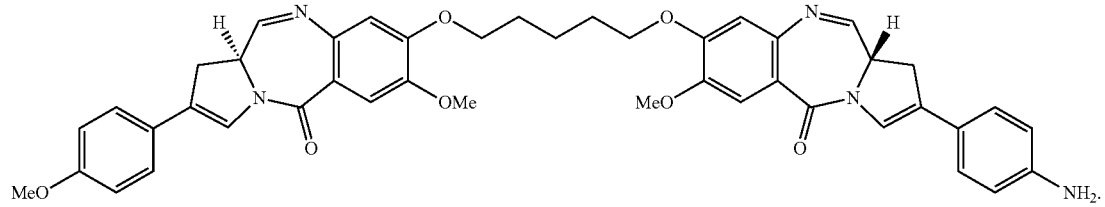
* * * * *

UNITED STATES PATENT AND TRADEMARK OFFICE
CERTIFICATE OF CORRECTION

PATENT NO. : 8,592,576 B2
APPLICATION NO. : 13/123327
DATED : November 26, 2013
INVENTOR(S) : Philip Wilson Howard et al.

It is certified that error appears in the above-identified patent and that said Letters Patent is hereby corrected as shown below:

In the Specification

Column 59, Line 16
-Please delete "30 μM", and insert --30 pM--.

Column 59, Line 45
-Please delete "Compound II", and insert --Compound 11--.
-Please delete "11.7 μM", and insert --11.7 pM--.

Signed and Sealed this
Thirty-first Day of March, 2015

Michelle K. Lee
*Director of the United States Patent and Trademark Office*

UNITED STATES PATENT AND TRADEMARK OFFICE
CERTIFICATE OF CORRECTION

PATENT NO.        : 8,592,576 B2                                          Page 1 of 1
APPLICATION NO.   : 13/123327
DATED             : November 26, 2013
INVENTOR(S)       : Howard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this
Twenty-second Day of September, 2015

Michelle K. Lee
*Director of the United States Patent and Trademark Office*